(12) United States Patent
Fuso et al.

(10) Patent No.: US 7,868,171 B2
(45) Date of Patent: *Jan. 11, 2011

(54) N-ALKOXY-4, 4-DIOXY-POLYALKYL-PIPERIDINES AS RADICAL POLYMERIZATION INITIATORS

(75) Inventors: Francesco Fuso, Therwil (CH); Wiebke Wunderlich, Bologna (IT); Andreas Kramer, Meyriez (CH); Jochen Fink, Nussloch (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/729,484

(22) Filed: Mar. 29, 2007

(65) Prior Publication Data

US 2007/0173570 A1    Jul. 26, 2007

Related U.S. Application Data

(62) Division of application No. 10/450,227, filed as application No. PCT/EP01/13071 on Nov. 12, 2001, now Pat. No. 7,235,663.

(51) Int. Cl.
*C07D 401/04* (2006.01)
*C08K 5/35* (2006.01)

(52) U.S. Cl. .......................................... 546/18; 524/95

(58) Field of Classification Search .................. 524/95
See application file for complete search history.

(56) References Cited

U.S. PATENT DOCUMENTS

| 4,105,626 | A | * | 8/1978 | Brunetti et al. | ............... | 524/99 |
| 4,581,429 | A | | 4/1986 | Solomon et al. | ............ | 526/220 |
| 4,921,962 | A | | 5/1990 | Galbo et al. | ................ | 546/184 |
| 6,353,107 | B1 | * | 3/2002 | Kramer et al. | ............... | 546/216 |
| 6,566,468 | B1 | * | 5/2003 | Fuso et al. | ................... | 526/220 |
| 7,228,613 | B2 | * | 6/2007 | Klobcic | ..................... | 29/564.4 |
| 2003/0065184 | A1 | | 4/2003 | Nesvadba et al. | ........... | 546/216 |
| 2008/0015276 | A1 | * | 1/2008 | Nesvadba et al. | ............. | 522/63 |

FOREIGN PATENT DOCUMENTS

| EP | 0467851 | 1/1992 |
| WO | 97/36894 | 10/1997 |
| WO | 99/46261 | 9/1999 |

* cited by examiner

*Primary Examiner*—Rita J Desai
(74) *Attorney, Agent, or Firm*—Tyler A. Steveson

(57) ABSTRACT

The present invention relates to selected glycidyl or carbonyl functional N-alkoxy-4,4-dioxy-polyalkyl-piperidine compounds forming an open chain or cyclic ketal structure, a polymerizable composition comprising a) at least one ethylenically unsaturated monomer and b) a glycidyl or carbonyl functional N-alkoxy-4,4-dioxy-polyalkyl-piperidine nitroxide initiator compound. Further aspects of the present invention are a process for polymerizing ethylenically unsaturated monomers and the use of glycidyl or carbonyl functional N-alkoxy-4,4-dioxy-polyalkyl-piperidine nitroxide initiators for radical polymerization.

1 Claim, No Drawings

N-ALKOXY-4, 4-DIOXY-POLYALKYL-PIPERIDINES AS RADICAL POLYMERIZATION INITIATORS

This application is a divisional of application Ser. No. 10/450,227 filed Jun. 11, 2003, now U.S. Pat. No. 7,235,663, which is a 371 of international app. No. PCT/EP 01/13071, filed Nov. 12, 2001, the contents of which applications are hereby incorporated by reference.

The present invention relates to selected glycidyl or carbonyl functional N-alkoxy-4,4-dioxy-polyalkyl-piperidine compounds forming an open chain or cyclic ketal structure, a polymerizable composition comprising a) at least one ethylenically unsaturated monomer and b) a glycidyl or carbonyl functional N-alkoxy-4,4-dioxy-polyalkyl-piperidine nitroxide initiator compound. Further aspects of the present invention are a process for polymerizing ethylenically unsaturated monomers and the use of glycidyl or carbonyl functional N-alkoxy-4,4-dioxy-polyalkyl-piperidine nitroxide initiators for radical polymerization.

The compounds of the present invention provide polymeric resin products having low polydispersity and the polymerization process proceeds with good monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O ● groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

The radical initiators, polymerization processes and resin products of the present invention have an additional glycidyl or carbonyl group, which can be used for further reactions. The resulting resins are useful in many applications.

The glycidyl or alkylcarbonyl group of the present initiators remains essentially unchanged during the radical polymerization reaction. Therefore the radical initiators of the present invention offer the possibility, after the radical polymerization is accomplished or stopped, to react the glycidyl group of the oligomers or polymers in a second step with nucleophiles such as alcohols, mercaptanes, amines, metal organic compounds or the like, thereby changing the properties of the oligomers or polymers.

The glycidyl group of the initiators can also be reacted in a first step for example by anionic polymerization in the presence of for example dicyandiamide, butyl-Lithium or other strong bases leading to oligomeric/polymeric radical initiators.

S. Kobatake et al, Macromolecules 1997, 30, 4238-4242 and in WO 97/36894 disclose the anionic polymerization of butadiene in the presence of compound (a) which contains a glycidyl group in a side chain. This compound acts as a terminating reagent for the anionic polymerization of butadiene.

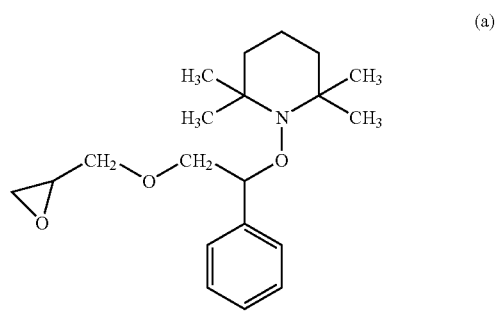

(a)

The resulting macromolecule can be further used as a macroinitiator for radical polymerization and for preparing block copolymers containing a poylbutadiene segment. Typical copolymers which can be produced are acrylnitrile/butadiene/styrene (ABS) copolymers.

The present invention provides initiators for radical polymerization which contain the glycidyl or alkylcarbonyl group attached to the phenyl group. The initiators show a high reactivity, good rates of polymerization and good monomer to polymer conversions.

The remaining glycidyl or carbonyl group is highly reactive towards nucleophiles and can readily be transformed into other chemical groups if desired.

The compounds of the present invention are also useful as terminating agents in the anionic polymerization of for example butadiene as described in WO 97/36894. With the instant compounds termination of anionic polymerization of for example butadiene proceeds fast and complete.

Glycidyl or carbonyl functional alkoxyamines containing a tetramethyl-piperidine group and their use as functionalized radical initiators/regulators have already been described in WO 99/46261. The instant compounds differ from those disclosed in WO 99/46261 in that they have a ketal structure in 4 position of the piperidine moiety. Such compounds and their use as polymerization initiators/regulators have neither been disclosed as specific compounds nor generically in the prior art.

It has now been found, that amongst those 2,2,6,6-tetraalkylpiperidines described in the prior art those are of particular value which are derivatives of 2,2,6,6 tetramethyl piperidine, 2,2 diethyl-6,6 dimethyl piperidine and of 2,6-diethyl-2,3,6-trimethyl piperidine which are substituted in the 4 position by two oxygen atoms forming an open chain or cyclic ketal structure.

The ketal structure in 4 position ensures high thermal stability which is important for storage, particularly at elevated temperatures. The ketal structure is thermally significantly more stable compared to the corresponding 4-oxo compound.

The compounds exhibit an unchanged initiating/regulating activity even after storage at elevated temperatures as for example used in conventional stability tests.

Another problem associated with nitroxyl or nitroxyl ether mediated free radical polymerization is the formation of a significant color of the resulting polymer. The compounds of the present invention which have a ketal structure in 4-position impart less color to the polymer compared to other prior art compounds of similar structure.

The steric hindrance introduced by the two diethyl groups instead of two methyl groups further leads to an optimized balance in terms of stability of the compounds, initiating activity and control of polymerization.

The particular substitution pattern in 2 and 6 position of the piperidine ring allows high monomer to polymer conversions in short times and low polydispersities which are generally below 2. High monomer to polymer conversions are even achieved with acrylates, such as ethyl- or butyl-acrylate. The temperature necessary to achieve high conversion in short times may be for example as low as 120° C.

The present invention provides compounds useful as initiators/regulators for controlled radical polymerization which in addition have a highly reactive functional group allowing polymer analogous reactions or anionic polymerization termination, which can be adjusted in their initiating/controlling efficiency by adjusting the steric hindrance at the nitrogen atom and which have an excellent storage stability and impart none or only little color to the final polymer.

The compounds of the present invention are novel and consequently one subject of the instant invention is a compound of formula Ia, IIa or IIIa (Ia)

(IIa)

(IIIa)

wherein

D is a group or a group $C(O)-R_{13}$;
$R_{13}$ is phenyl or $C_1-C_{18}$alkyl;
m is 1, 2 or 3;
n is 1 or 2;
if n is 1
Y and Y' are independently $C_1-C_{12}$alkyl, $C_3-C_{12}$alkenyl, $C_3-C_{12}$alkinyl, $C_5-C_8$cycloalkyl, phenyl, naphthyl, $C_7-C_9$phenylalkyl; or Y and Y' together form one of the bivalent groups $-C(R_1)(R_2)-CH(R_3)-$, $CH(R_1)-CH_2-C(R_2)(R_3)-$, $-CH(R_2)-CH_2-C(R_1)(R_3)-$, $-CH_2-C(R_1)(R_2)-CH(R_3)-$, o-phenylene, 1,2-cyclohexyliden, $-CH_2-CH=CH-CH_2-$ or wherein
$R_1$ is hydrogen, $C_1-C_{12}$alkyl, COOH, COO$-(C_1-C_{12})$alkyl or $CH_2OR_4$;
$R_2$ and $R_3$ are independently hydrogen, methyl ethyl, COOH or COO$-(C_1-C_{12})$alkyl;
$R_4$ is hydrogen, $C_1-C_{12}$alkyl, benzyl, or a monovalent acyl residue derived from an aliphatic, cycloaliphatic or aromatic monocarboxylic acid having up to 18 carbon atoms;
if n is 2
Y and Y' together form one of the tetravalent groups wherein
Q is a bisacyl residue which is derived from a $C_2-C_{12}$dicarboxylic acid or $C_1-C_{12}$alkylene;
Z is $C_1-C_{12}$alkylene;
the $R_{12}$ are independently of each other H or $CH_3$.

$C_1-C_{18}$alkyl can be linear or branched. Examples are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, heptadecyl or octadecyl.

Alkenyl having from 3 to 12 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl, isododecenyl.

Alkinyl having from 3 to 12 carbon atoms is a branched or unbranched radical, for example propinyl ($-CH_2-C\equiv CH$), 2-butinyl, 3-butinyl, n-2-octinyl or n-2-dodecinyl.

Examples of alkoxy are methoxy, ethoxy, propoxy, isopropoxy, butoxy, isobutoxy, pentoxy, isopentoxy, hexoxy, heptoxy or octoxy.

$C_7-C_9$phenylalkyl is for example benzyl, α-methylbenzyl, α,α-dimethylbenzyl or 2-phenylethyl, benzyl is preferred.

$C_1$-$C_{12}$alkylene is a branched or unbranched radical, for example methylene, ethylene, propylene, trimethylene, tetramethylene, pentamethylene, hexamethylene, heptamethylene, octamethylene, decamethylene or dodecamethylene.

$C_5$-$C_8$cycloalkyl is for example cyclopentyl, cyclohexyl, cycloheptyl, methylcyclopentyl or cyclooctyl.

Examples of a monocarboxylic acid having up to 18 carbon atoms are formic acid, acetic acid, propionic acid, the isomers of valeric acid, methyl ethyl acetic acid, trimethyl acetic acid, capronic acid, lauric acid or stearic acid. Examples for unsaturated aliphatic acids are acrylic acid, methacrylic acid, crotonic acid, linolic acid and oleic acid.

Typical examples of cycloaliphatic carboxylic acids are cyclohexane carboxylic acid or cyclopentane carboxylic acid.

Examples of aromatic carboxylic acids are benzoic acid, salicylic acid or cinnamic acid.

Examples of dicarboxylic acids are oxalic acid, malonic acid, succinic acid, glutaric acid, adipic acid, sebatic acid, fumaric acid, maleic acid, phthalic acid, isophthalic acid, terephthalic acid.

Preferred is a compound wherein in the formulae Ia, IIa or IIIa D is a group

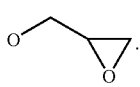

Particularly preferred is a compound of formula Ia, IIa or IIIa wherein

D is a group

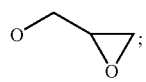

m is 1;
n is 1;
Y and Y' are independently $C_1$-$C_{12}$alkyl, $C_3$-$C_{12}$alkenyl, phenyl or benzyl; or
Y and Y' together form one of the bivalent groups —C($R_1$)($R_2$)—CH($R_3$)—, CH($R_1$)—CH$_2$—C($R_2$)($R_3$)—, —CH($R_2$)—CH$_2$—C($R_1$)($R_3$)—, —CH$_2$—C($R_1$)($R_2$)—CH($R_3$)—, —CH$_2$—CH=CH—CH$_2$— or;

wherein
$R_1$ is hydrogen, $C_1$-$C_{12}$alkyl, COO—($C_1$-$C_{12}$)alkyl or CH$_2$O$R_4$;
$R_2$ and $R_3$ are independently hydrogen, methyl ethyl, or COO—($C_1$-$C_{12}$)alkyl;
$R_4$ is hydrogen, $C_1$-$C_{12}$alkyl, benzyl, or a monovalent acyl residue derived from an aliphatic, cycloaliphatic or aromatic monocarboxylic acid having up to 12 carbon atoms and one of the $R_{12}$ is hydrogen and the other is methyl.

More preferred is a compound of formula Ia, IIa or IIIa wherein

D is a group

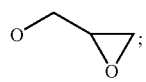

m is 1;
n is 1;
Y and Y' together form one of the bivalent groups —CH$_2$—C($R_1$)($R_2$)—CH($R_3$)— wherein
$R_1$ is hydrogen, methyl or ethyl;
$R_2$ and $R_3$ are independently hydrogen, methyl ethyl, or COO—($C_1$-$C_{12}$)alkyl; and
one of the $R_{12}$ hydrogen and the other is methyl.

Especially preferred is a compound of formula IIIa.

Specifically preferred compounds are listed in Tables 1, 2 and 3.

TABLE 1

1.) 2,6-Diethyl-4,4-dimethoxy-2,3,6-trimethyl-1-[1-(4-oxiranylmethoxy-phenyl)-ethoxy]-piperidine

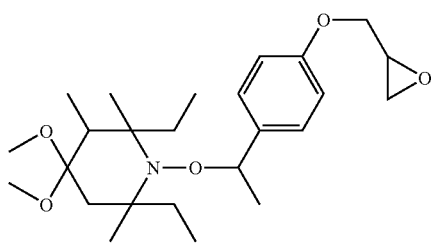

2.) 4,4-Diethoxy-2,6-diethyl-2,3,6-trimethyl-1-[1-(4-oxiranylmethoxy-phenyl)-ethoxy]-piperidine

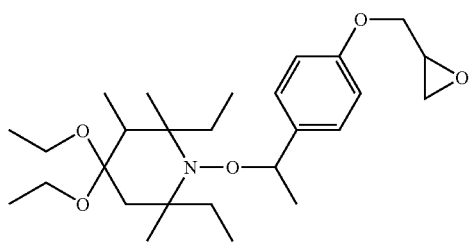

TABLE 1-continued

3.) 2,6-Diethyl-2,3,6-trimethyl-1-[1-(4-oxiranylmethoxy-phenyl)-ethoxy]-4,4-dipropoxy-piperidine

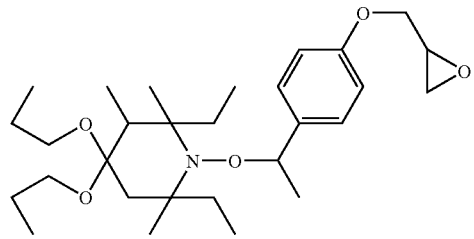

4.) 4,4-Dibutoxy-2,6-diethyl-2,3,6-trimethyl-1-[1-(4-oxiranylmethoxy-phenyl)-ethoxy]-piperidine

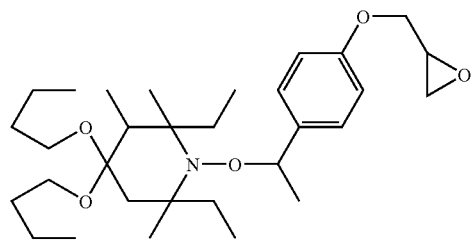

5.) 2,6-Diethyl-4,4-diisobutoxy-2,3,6-trimethyl-1-[1-(4-oxiranylmethoxy-phenyl)-ethoxy]-piperidine

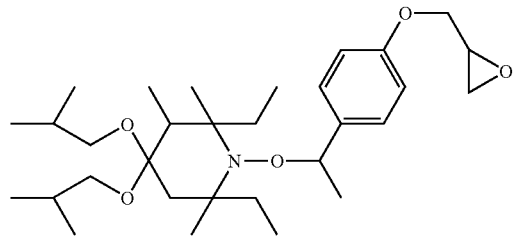

6.) 2,6-Diethyl-2,3,6-trimethyl-4,4-bis-octyloxy-1-[1-(4-oxiranylmethoxy-phenyl)-ethoxy]-piperidine

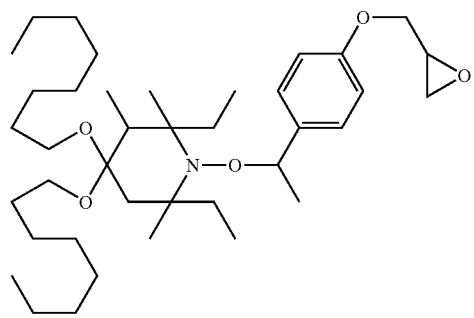

7.) 4,4-Bis-allyloxy-2,6-diethyl-2,3,6-trimethyl-1-[1-(4-oxiranylmethoxy-phenyl)-ethoxy]-piperidine

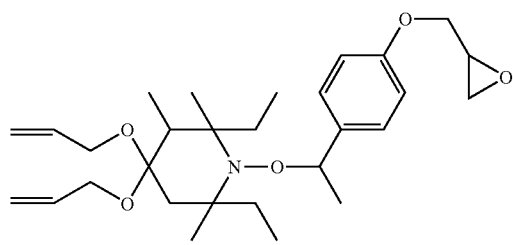

TABLE 1-continued

8.) 4,4-Bis-cyclohexyloxy-2,6-diethyl-2,3,6-trimethyl-1-[1-(4-oxiranylmethoxy-phenyl)-ethoxy]-piperidine

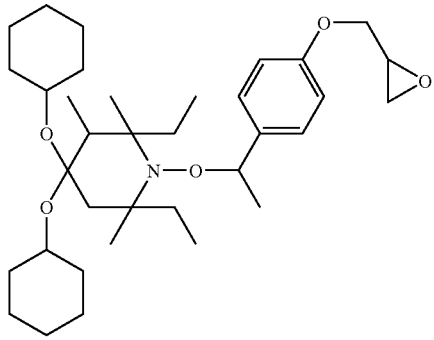

9.) 4,4-Bis-benzyloxy-2,6-diethyl-2,3,6-trimethyl-1-[1-(4-oxiranylmethoxy-phenyl)-ethoxy]-piperidine

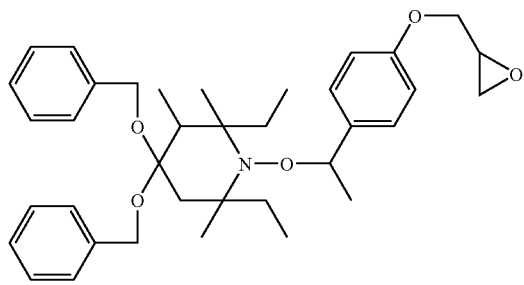

10.) 7,9-Diethyl-6,7,9-trimethyl-8-[1-(4-oxiranylmethoxy-phenyl)-ethoxy]-1,4-dioxa-8-aza-spiro[4.5]decane

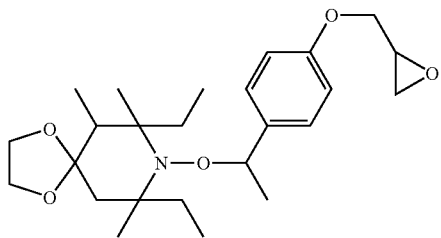

11.) 7,9-Diethyl-2,6,7,9-tetramethyl-8-[1-(4-oxiranylmethoxy-phenyl)-ethoxy]-1,4-dioxa-8-aza-spiro[4.5]decane

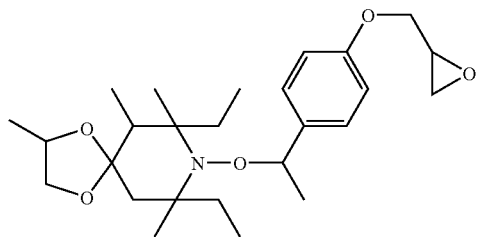

12.) 2,7,9-Triethyl-6,7,9-trimethyl-8-[1-(4-oxiranylmethoxy-phenyl)-ethoxy]-1,4-dioxa-8-aza-spiro[4.5]decane

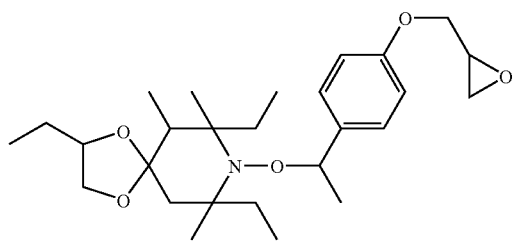

TABLE 1-continued

13.) 7,9-Diethyl-6,7,9-trimethyl-8-[1-(4-oxiranylmethoxy-phenyl)-ethoxy]-2-propyl-1,4-dioxa-8-aza-spiro[4.5]decane

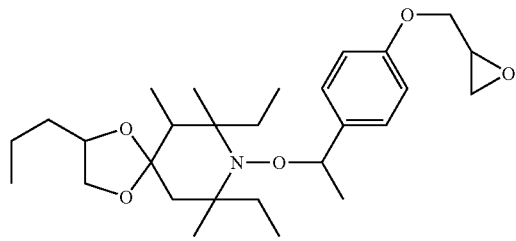

14.) 2-Butyl-7,9-diethyl-6,7,9-trimethyl-8-[1-(4-oxiranylmethoxy-phenyl)-ethoxy]-1,4-dioxa-8-aza-spiro[4.5]decane

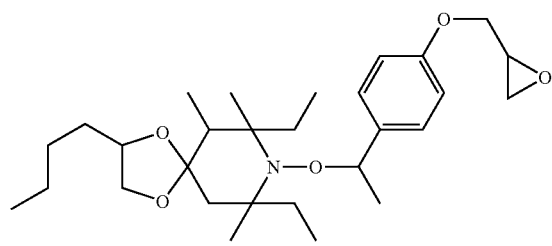

15.) 7,9-Diethyl-6,7,9-trimethyl-2-octyl-8-[1-(4-oxiranylmethoxy-phenyl)-ethoxy]-1,4-dioxa-8-aza-spiro[4.5]decane

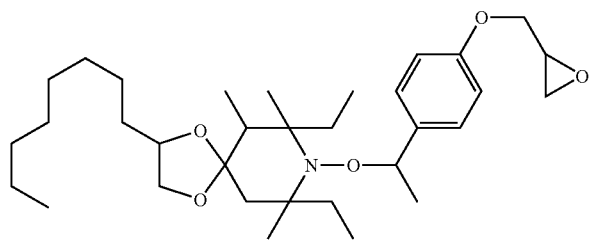

16.) 2-Decyl-7,9-diethyl-6,7,9-trimethyl-8-[1-(4-oxiranylmethoxy-phenyl)-ethoxy]-1,4-dioxa-8-aza-spiro[4.5]decane

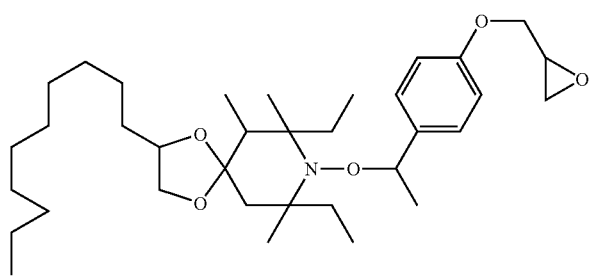

17.) 2-Dodecyl-7,9-diethyl-6,7,9-trimethyl-8-[1-(4-oxiranylmethoxy-phenyl)-ethoxy]-1,4-dioxa-8-aza-spiro[4.5]decane

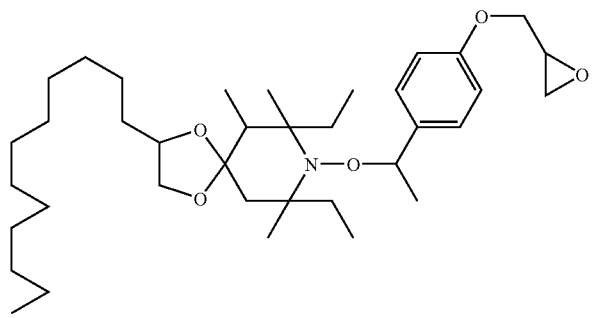

TABLE 1-continued

18.) {7,9-Diethyl-6,7,9-trimethyl-8-[1-(4-oxiranylmethoxy-phenyl)-ethoxy]-1,4-dioxa-8-aza-spiro[4.5]dec-2-yl}-methanol

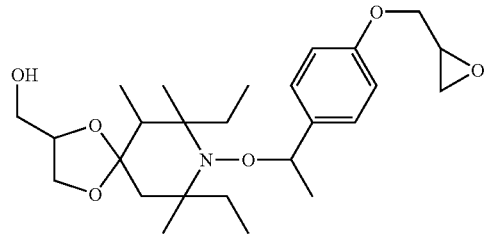

19.) Acetic acid 7,9-diethyl-6,7,9-trimethyl-8-[1-(4-oxiranylmethoxy-phenyl)-ethoxy]-1,4-dioxa-8-aza-spiro[4.5]dec-2-ylmethyl ester

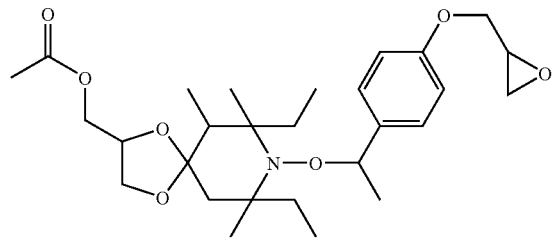

20.) Octadecanoic acid 7,9-diethyl-6,7,9-trimethyl-8-[1-(4-oxiranylmethoxy-phenyl)-ethoxy]-1,4-dioxa-8-aza-spiro[4.5]dec-2-ylmethyl ester

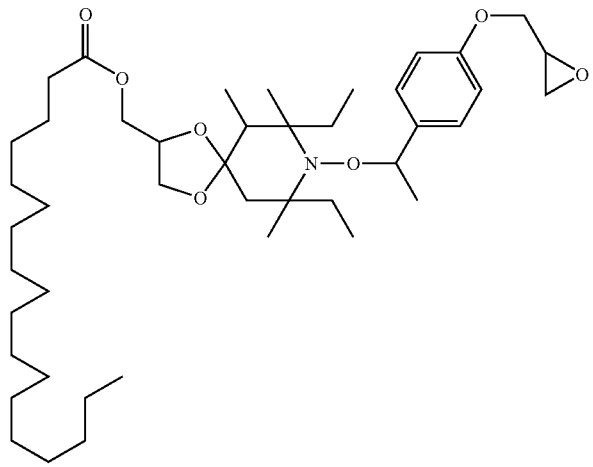

21.) Benzoic acid 7,9-diethyl-6,7,9-trimethyl-8-[1-(4-oxiranylmethoxy-phenyl)-ethoxy]-1,4-dioxa-8-aza-spiro[4.5]dec-2-ylmethyl ester

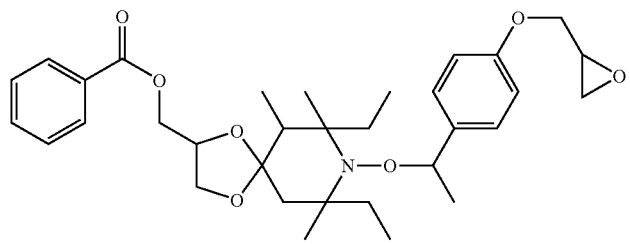

22.) 7,9-Diethyl-2-methoxymethyl-6,7,9-trimethyl-8-[1-(4-oxiranylmethoxy-phenyl)-ethoxy]-1,4-dioxa-8-aza-spiro[4.5]decane

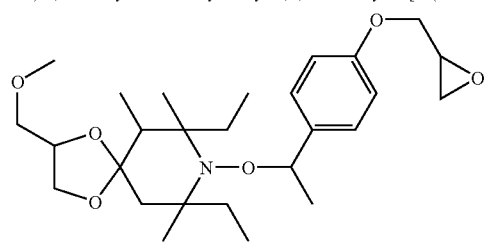

TABLE 1-continued

23.) 2-Cyclohexyloxymethyl-7,9-diethyl-6,7,9-trimethyl-8-[1-(4-oxiranylmethoxy-phenyl)-ethoxy]-1,4-dioxa-8-aza-spiro[4.5]decane

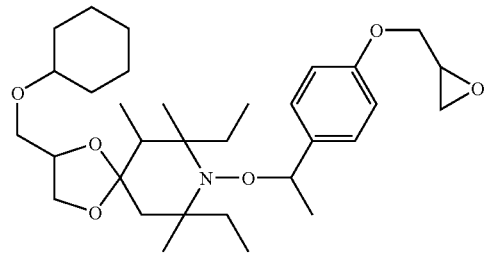

24.) 2-Benzyloxymethyl-7,9-diethyl-6,7,9-trimethyl-8-[1-(4-oxiranylmethoxy-phenyl)-ethoxy]-1,4-dioxa-8-aza-spiro[4.5]decane

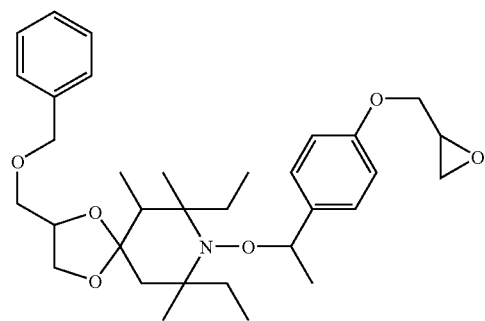

25.) Octanedioic acid bis-{7,9-diethyl-6,7,9-trimethyl-8-[1-(4-oxiranylmethoxy-phenyl)-ethoxy]-1,4-dioxa-8-aza-spiro[4.5]dec-2-ylmethyl}ester

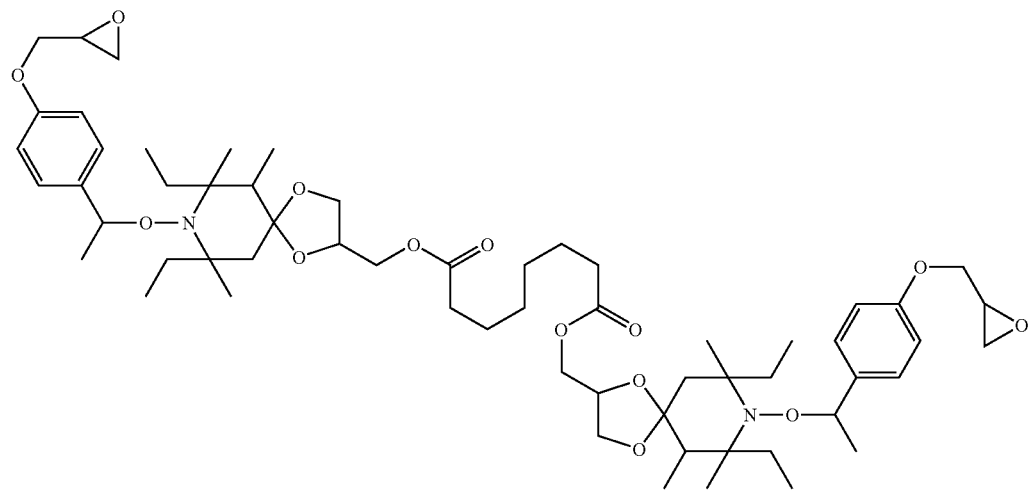

26.) Terephthalic acid bis-{7,9-diethyl-6,7,9-trimethyl-8-[1-(4-oxiranylmethoxy-phenyl)-ethoxy]-1,4-dioxa-8-aza-spiro[4.5]dec-2-ylmethyl}ester

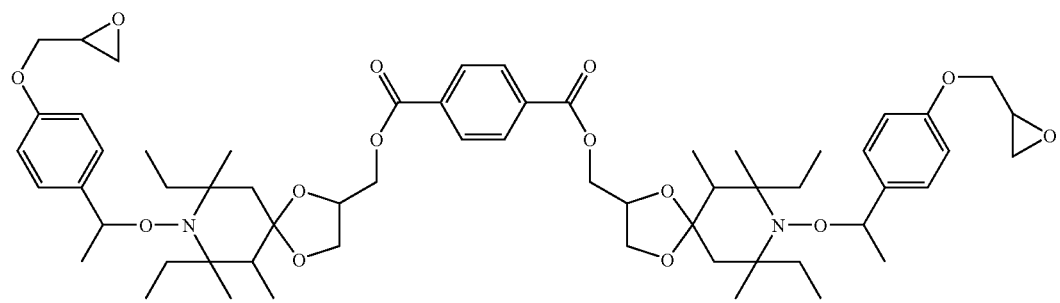

TABLE 1-continued

27.) 1',4'-Bis-{7,9-diethyl-6,7,9-trimethyl-8-(1-(4-oxiranylmethoxy-phenyl)-ethoxy)-1,4-dioxa-8-aza-spiro[4.5]dec-2-ylmethyl}-oxybutane

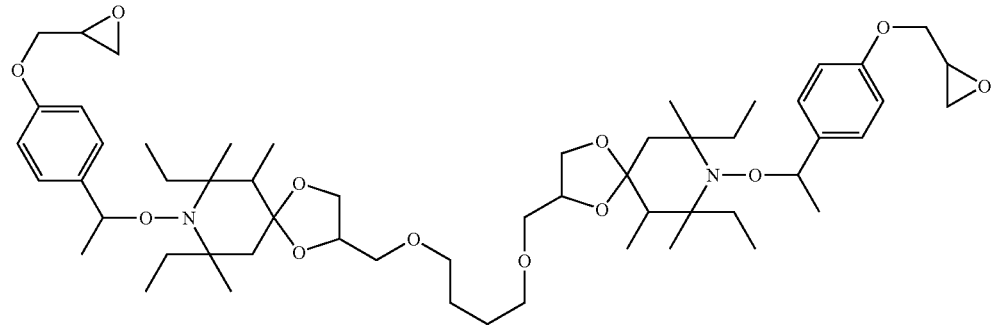

28.) 7,9-Diethyl-2,2,6,7,9-pentamethyl-8-[1-(4-oxiranylmethoxy-phenyl)-ethoxy]-1,4-dioxa-8-aza-spiro[4.5]decane

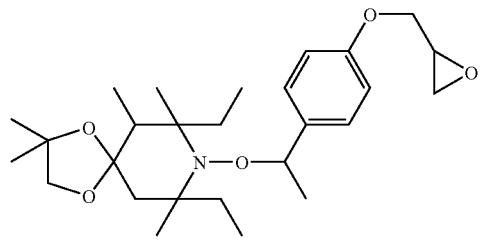

29.) 7,9-Diethyl-2,3,6,7,9-pentamethyl-8-[1-(4-oxiranylmethoxy-phenyl)-ethoxy]-1,4-dioxa-8-aza-spiro[4.5]decane

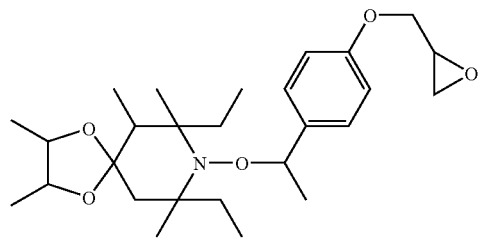

30.) 4,4-(o-Phenylendioxy)-2,6-diethyl-2,3,6-trimethyl-1-[1'-(4'-oxiranylmethoxy-phenyl)-ethoxy]-piperidine

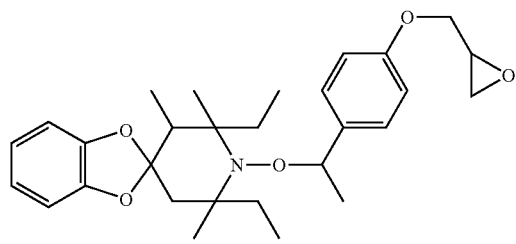

31.) 4,4-(1',2'-cyclohexylendioxy)-2,6-diethyl-2,3,6-trimethyl-1-[1''-(4''-oxiranylmethoxy-phenyl)-ethoxy]-piperidine

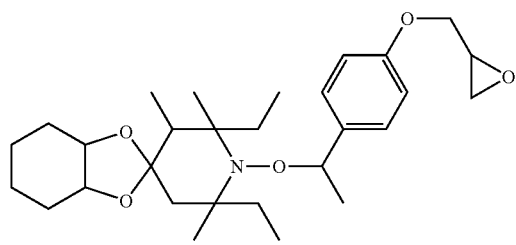

TABLE 1-continued

32.) 7,9-Diethyl-6,7,9-trimethyl-8-[1-(4-oxiranylmethoxy-phenyl)-ethoxy]-1,4-dioxa-8-aza-spiro[4.5]decane-2,3-dicarboxylic acid dimethyl ester

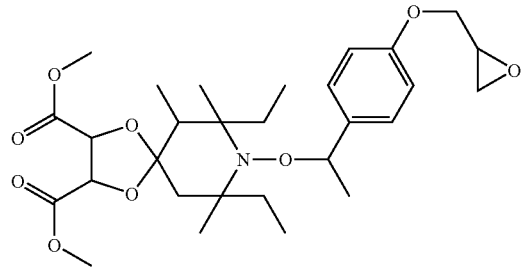

33.) 8,10-Diethyl-7,8,10-trimethyl-9-[1-(4-oxiranylmethoxy-phenyl)-ethoxy]-1,5-dioxa-9-aza-spiro[5.5]undecane

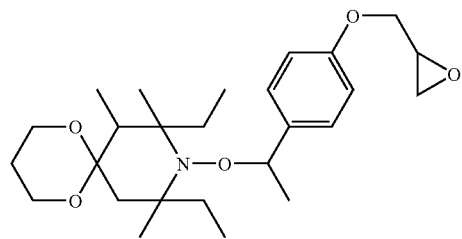

34.) 8,10-Diethyl-3,3,7,8,10-pentamethyl-9-[1-(4-oxiranylmethoxy-phenyl)-ethoxy]-1,5-dioxa-9-aza-spiro[5.5]undecane

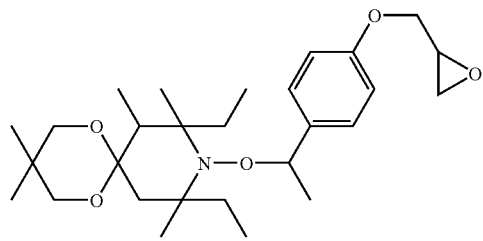

35.) 3,8,10-Triethyl-3,7,8,10-tetramethyl-9-[1-(4-oxiranylmethoxy-phenyl)-ethoxy]-1,5-dioxa-9-aza-spiro[5.5]undecane

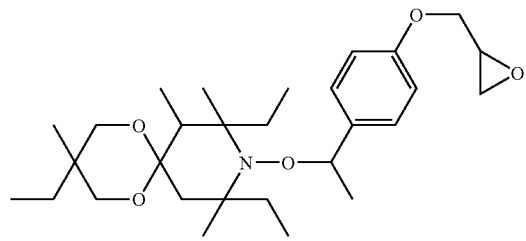

36.) 3,3,8,10-Tetraethyl-7,8,10-trimethyl-9-[1-(4-oxiranylmethoxy-phenyl)-ethoxy]-1,5-dioxa-9-aza-spiro[5.5]undecane

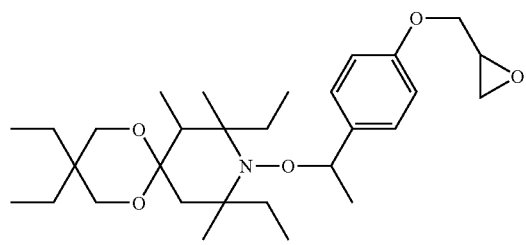

TABLE 1-continued

37.) 8,10-Diethyl-3,7,8,10-tetramethyl-9-[1-(4-oxiranylmethoxy-phenyl)-ethoxy]-3-propyl-1,5-dioxa-9-aza-spiro[5.5]undecane

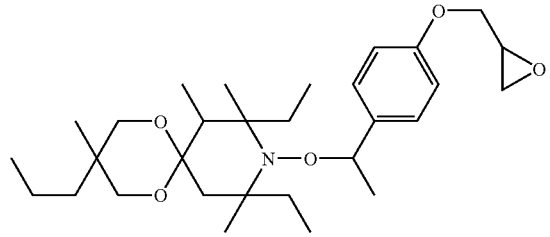

38.) 3-Butyl-3,8,10-triethyl-7,8,10-trimethyl-9-[1-(4-oxiranylmethoxy-phenyl)-ethoxy]-1,5-dioxa-9-aza-spiro[5.5]undecane

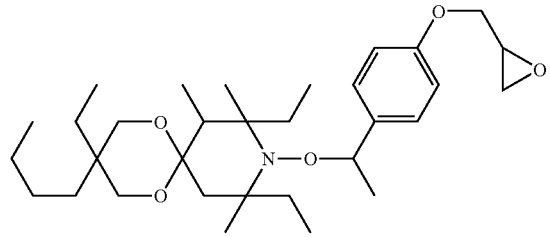

39.) 2,4-Diethyl-1,2,4-trimethyl-3-[1-(4-oxiranylmethoxy-phenyl)-ethoxy]-7,16-dioxa-3-aza-dispiro[5.2.5.2]hexadec-11-ene

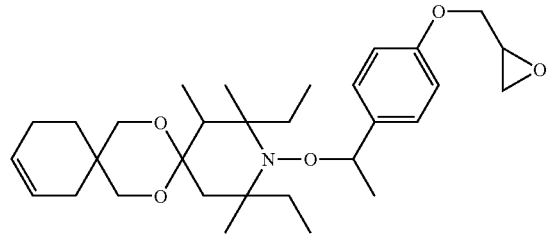

40.) {8,10-Diethyl-3,7,8,10-tetramethyl-9-[1-(4-oxiranylmethoxy-phenyl)-ethoxy]-1,5-dioxa-9-aza-spiro[5.5]undec-3-yl}-methanol

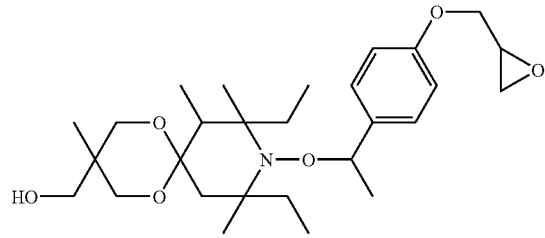

41.) {3,8,10-Triethyl-7,8,10-trimethyl-9-[1-(4-oxiranylmethoxy-phenyl)-ethoxy]-1,5-dioxa-9-aza-spiro[5.5]undec-3-yl}-methanol

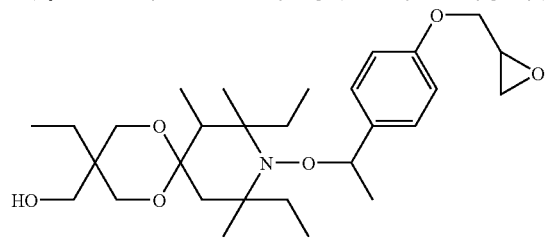

42.) 8,10-Diethyl-3-methoxymethyl-3,7,8,10-tetramethyl-9-[1-(4-oxiranylmethoxy-phenyl)-ethoxy]-1,5-dioxa-9-aza-spiro[5.5]undecane

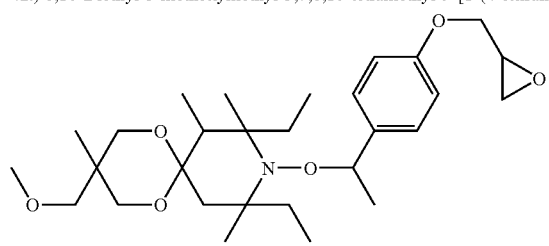

TABLE 1-continued

43.) 3-Cyclohexyloxymethyl-8,10-diethyl-3,7,8,10-tetramethyl-9-[1-(4-oxiranylmethoxy-phenyl)-ethoxy]-1,5-dioxa-9-aza-spiro[5.5]undecane

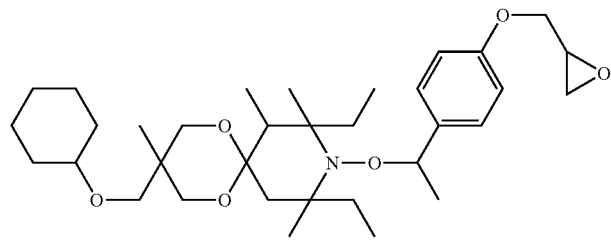

44.) 3-Benzyloxymethyl-8,10-diethyl-3,7,8,10-tetramethyl-9-[1-(4-oxiranylmethoxy-phenyl)-ethoxy]-1,5-dioxa-9-aza-spiro[5.5]undecane

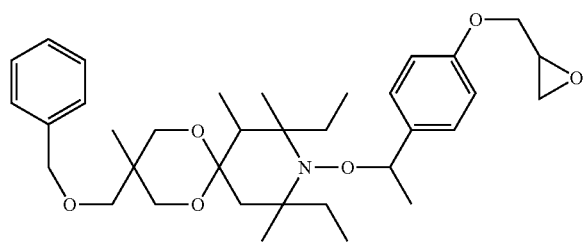

45.) Acetic acid 8,10-diethyl-3,7,8,10-tetramethyl-9-[1-(4-oxiranylmethoxy-phenyl)-ethoxy]-1,5-dioxa-9-aza-spiro[5.5]undec-3-ylmethyl ester

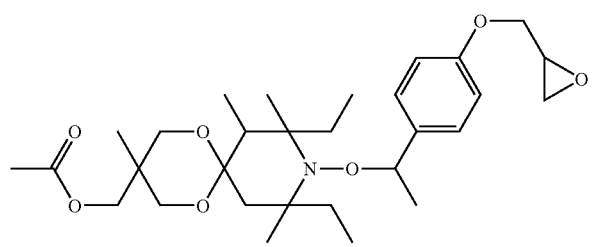

46.) Octanedioic acid bis-{8,10-diethyl-3,7,8,10-tetramethyl-9-[1-(4-oxiranylmethoxy-phenyl)-ethoxy]-1,5-dioxa-9-aza-spiro[5.5]undec-3-ylmethyl} ester

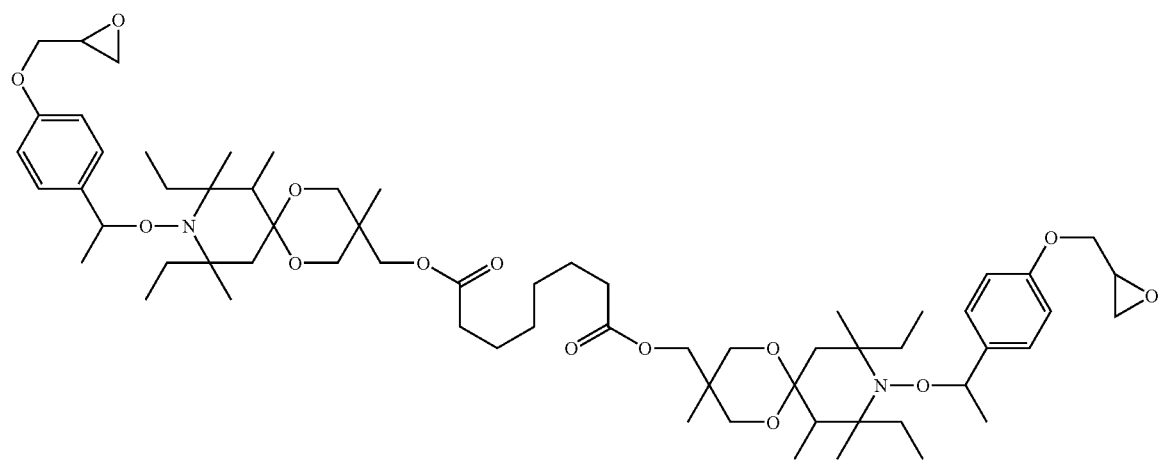

47.) 1',6'-Bis-{3,8,10-triethyl-7,8,10-trimethyl-9-[1-(4-oxiranylmethoxy-phenyl)-ethoxy]-1,5-dioxa-9-aza-spiro[5.5]undec-3-ylmethyl}-oxyhexane

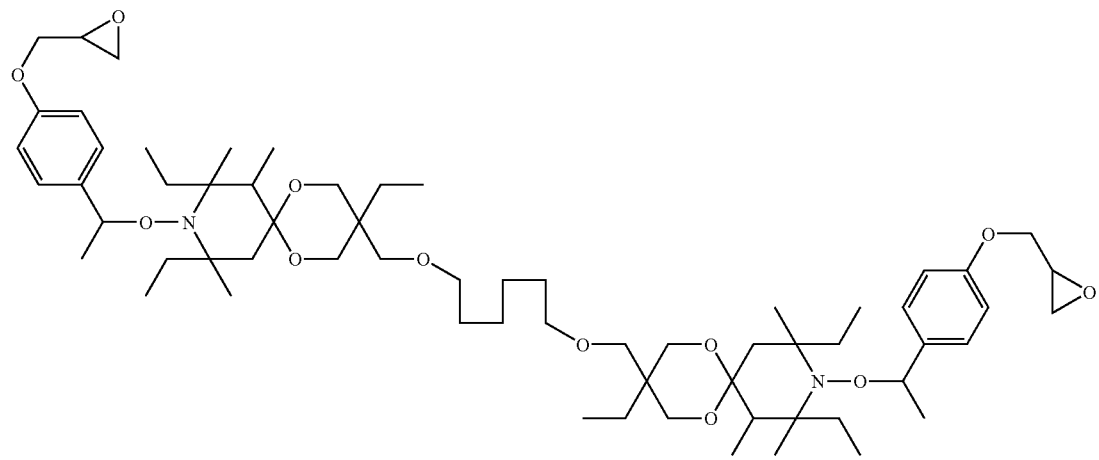

48.) 8,10-Diethyl-3,7,8,10-tetramethyl-9-[1-(4-oxiranylmethoxy-phenyl)-ethoxy]-1,5-dioxa-9-aza-spiro[5.5]undecane-3-carboxylic acid methyl ester

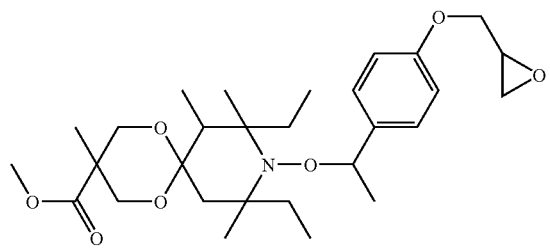

49.) 8,10-Diethyl-7,8,10-trimethyl-9-[1-(4-oxiranylmethoxy-phenyl)-ethoxy]-1,5-dioxa-9-aza-spiro[5.5]undecane-3,3-dicarboxylic acid diethyl ester

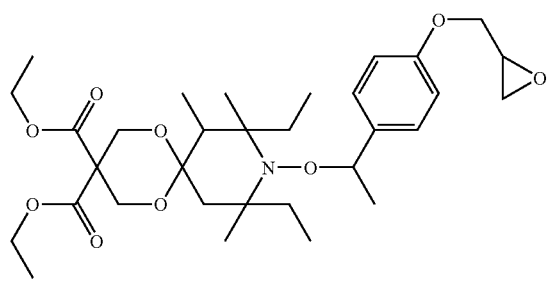

50.) 3,3-Bis-{8,10-diethyl-7,8,10-trimethyl-9-[1-(4-oxiranylmethoxy-phenyl)-ethoxy]-1,5-dioxa-9-aza}-spiro[5.5]undecane

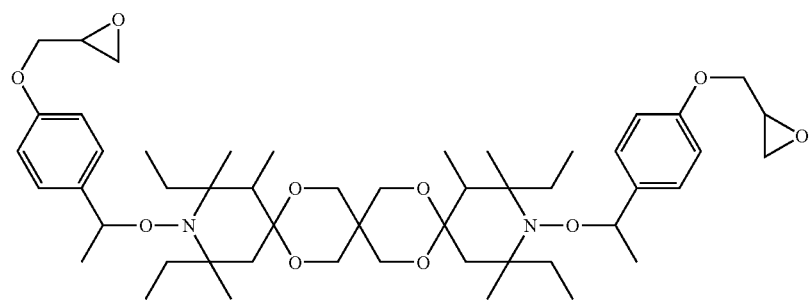

TABLE 1-continued

51.) 2,4-Diethyl-1,2,4-trimethyl-3-[1-(4-oxiranylmethoxy-phenyl)-ethoxy]-7,12-dioxa-3-aza-spiro[5.6]dodec-9-ene

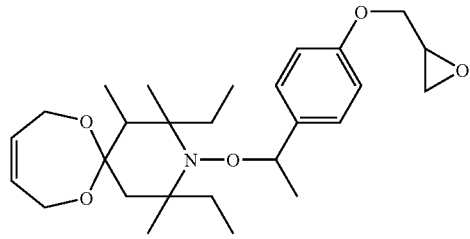

TABLE 2

1.) 2,2-Diethyl-4,4-dimethoxy-6,6-dimethyl-1-[1-(4-oxiranylmethoxy-phenyl)-ethoxy]-piperidine

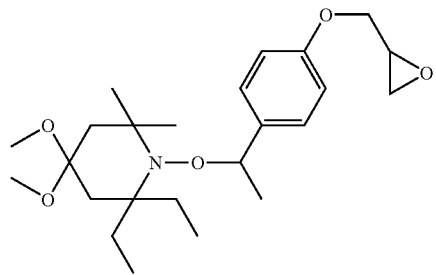

2.) 4,4-Diethoxy-2,2-diethyl-6,6-dimethyl-1-[1-(4-oxiranylmethoxy-phenyl)-ethoxy]-piperidine

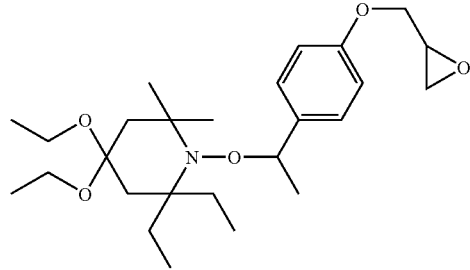

3.) 2,2-Diethyl-6,6-dimethyl-1-[1-(4-oxiranylmethoxy-phenyl)-ethoxy]-4,4-dipropoxy-piperidine

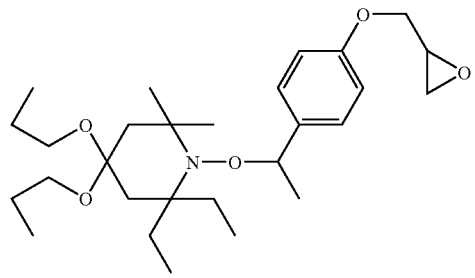

4.) 4,4-Dibutoxy-2,2-diethyl-6,6-dimethyl-1-[1-(4-oxiranylmethoxy-phenyl)-ethoxy]-piperidine

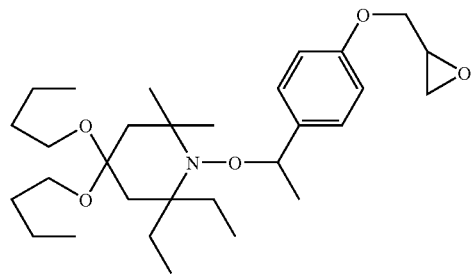

TABLE 2-continued

5.) 2,2-Diethyl-4,4-diisobutoxy-6,6-dimethyl-1-[1-(4-oxiranylmethoxy-phenyl)-ethoxy]-piperidine

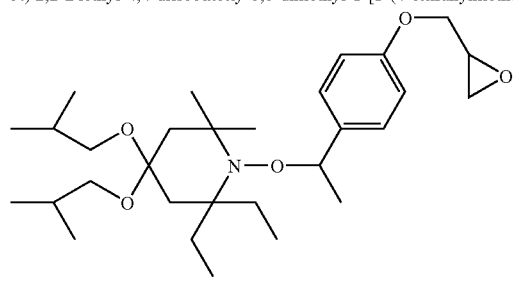

6.) 2,2-Diethyl-6,6-dimethyl-4,4-bis-octyloxy-1-[1-(4-oxiranylmethoxy-phenyl)-ethoxy]-piperidine

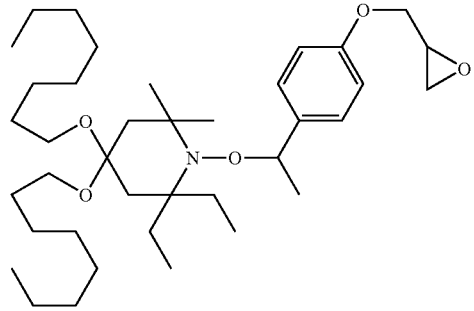

7.) 4,4-Bis-allyloxy-2,2-diethyl-6,6-dimethyl-1-[1-(4-oxiranylmethoxy-phenyl)-ethoxy]-piperidine

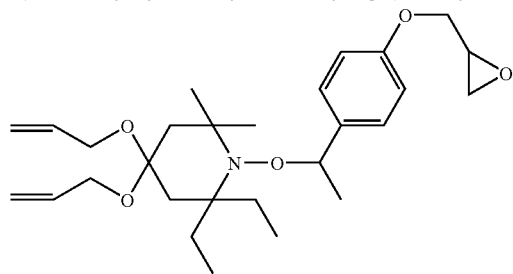

8.) 4,4-Bis-cyclohexyloxy-2,2-diethyl-6,6-dimethyl-1-[1-(4-oxiranylmethoxy-phenyl)-ethoxy]-piperidine

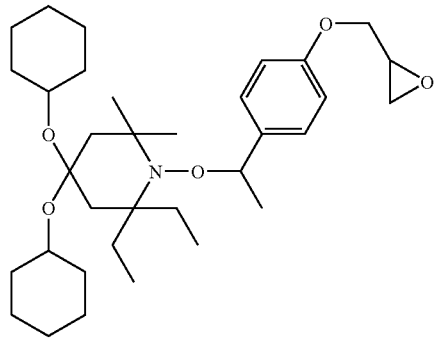

9.) 4,4-Bis-benzyloxy-2,2-diethyl-6,6-dimethyl-1-[1-(4-oxiranylmethoxy-phenyl)-ethoxy]-piperidine

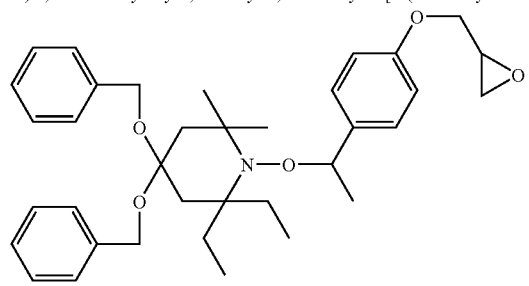

TABLE 2-continued

10.) 7,7-Diethyl-9,9-dimethyl-8-[1-(4-oxiranylmethoxy-phenyl)-ethoxy]-1,4-dioxa-8-aza-spiro[4.5]decane

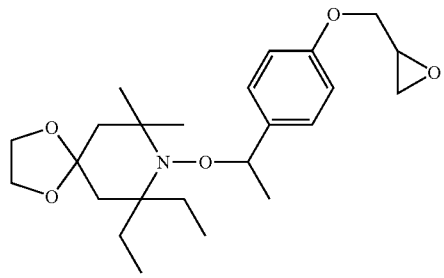

11.) 7,7-Diethyl-2,9,9-trimethyl-8-[1-(4-oxiranylmethoxy-phenyl)-ethoxy]-1,4-dioxa-8-aza-spiro[4.5]decane

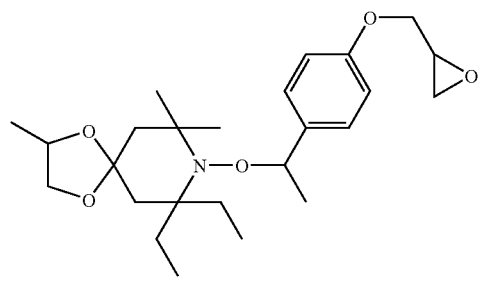

12.) 2,7,7-Triethyl-9,9-dimethyl-8-[1-(4-oxiranylmethoxy-phenyl)-ethoxy]-1,4-dioxa-8-aza-spiro[4.5]decane

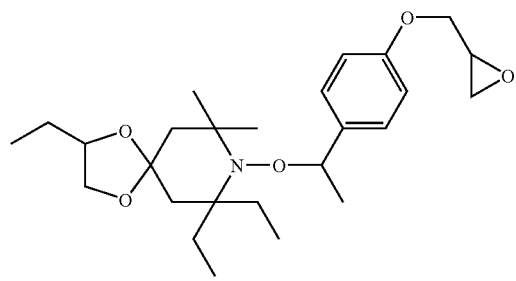

13.) 7,7-Diethyl-9,9-dimethyl-8-[1-(4-oxiranylmethoxy-phenyl)-ethoxy]-2-propyl-1,4-dioxa-8-aza-spiro[4.5]decane

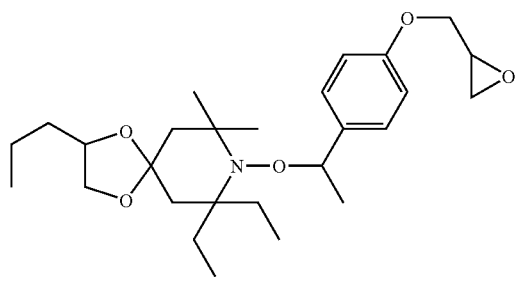

14.) 2-Butyl-7,7-diethyl-9,9-dimethyl-8-[1-(4-oxiranylmethoxy-phenyl)-ethoxy]-1,4-dioxa-8-aza-spiro[4.5]decane

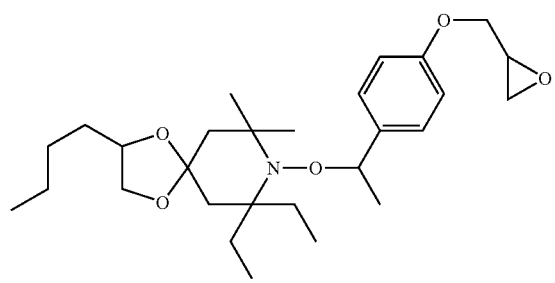

TABLE 2-continued

15.) 7,7-Diethyl-9,9-dimethyl-2-octyl-8-[1-(4-oxiranylmethoxy-phenyl)-ethoxy]-1,4-dioxa-8-aza-spiro[4.5]decane

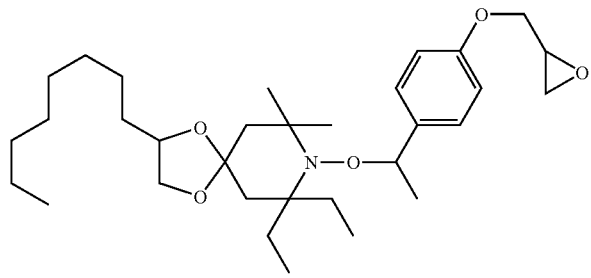

16.) 2-Decyl-7,7-diethyl-9,9-dimethyl-8-[1-(4-oxiranylmethoxy-phenyl)-ethoxy]-1,4-dioxa-8-aza-spiro[4.5]decane

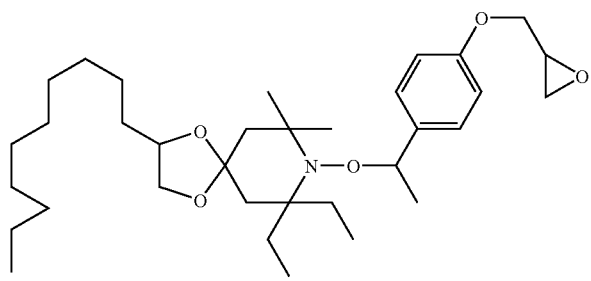

17.) 2-Dodecyl-7,7-diethyl-9,9-dimethyl-8-[1-(4-oxiranylmethoxy-phenyl)-ethoxy]-1,4-dioxa-8-aza-spiro[4.5]decane

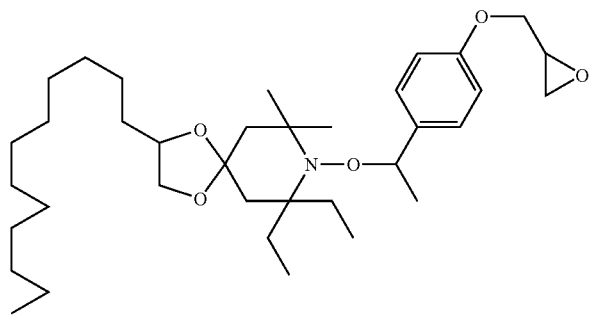

18.) {7,7-Diethyl-9,9-dimethyl-8-[1-(4-oxiranylmethoxy-phenyl)-ethoxy]-1,4-dioxa-8-aza-spiro[4.5]dec-2-yl}-methanol

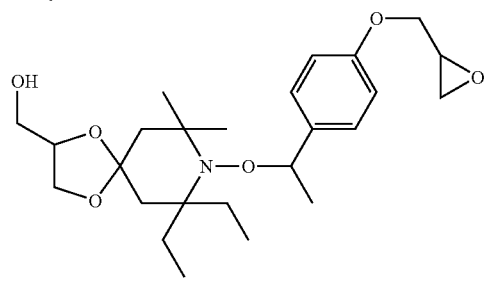

19.) Acetic acid 7,7-diethyl-9,9-dimethyl-8-[1-(4-oxiranylmethoxy-phenyl)-ethoxy]-1,4-dioxa-8-aza-spiro[4.5]dec-2-ylmethyl ester

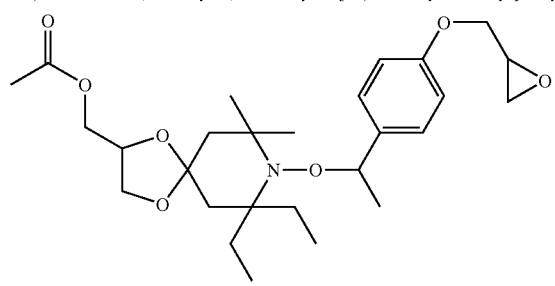

TABLE 2-continued

20.) Octadecanoic acid 7,7-diethyl-9,9-dimethyl-8-[1-(4-oxiranylmethoxy-phenyl)-ethoxy]-1,4-dioxa-8-aza-spiro[4.5]dec-2-ylmethyl ester

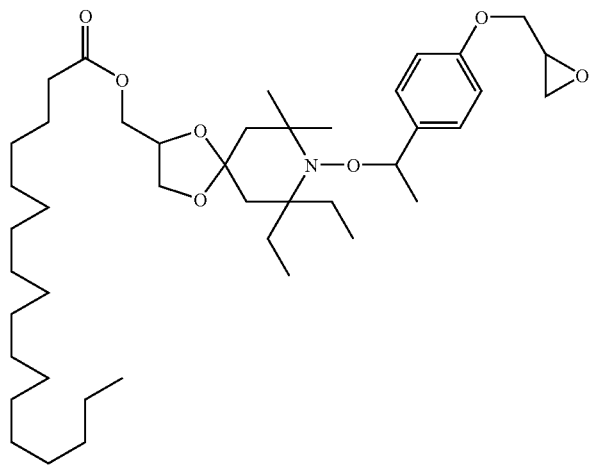

21.) Benzoic acid 7,7-diethyl-9,9-dimethyl-8-[1-(4-oxiranylmethoxy-phenyl)-ethoxy]-1,4-dioxa-8-aza-spiro[4.5]dec-2-ylmethyl ester

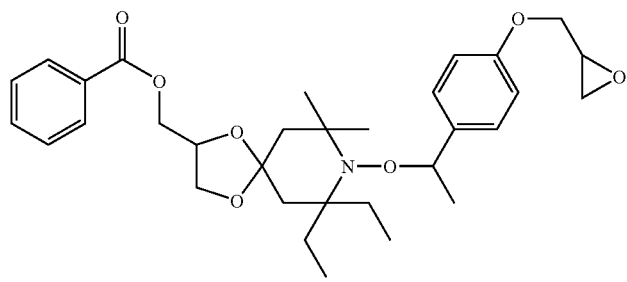

22.) 7,7-Diethyl-2-methoxymethyl-9,9-dimethyl-8-[1-(4-oxiranylmethoxy-phenyl)-ethoxy]-1,4-dioxa-8-aza-spiro[4.5]decane

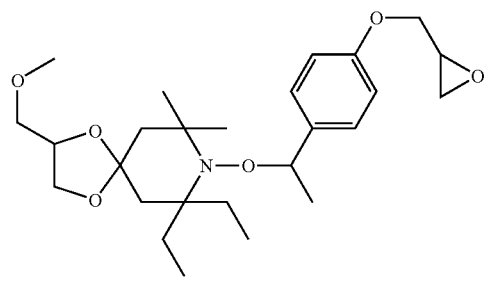

23.) 2-Cyclohexyloxymethyl-7,7-diethyl-9,9-dimethyl-8-[1-(4-oxiranylmethoxy-phenyl)-ethoxy]-1,4-dioxa-8-aza-spiro[4.5]decane

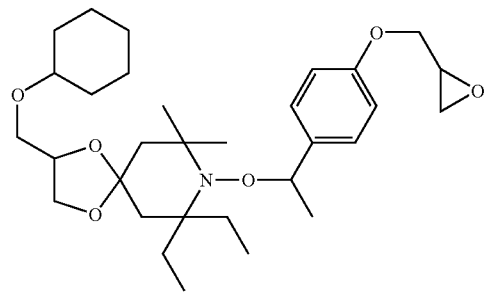

TABLE 2-continued

24.) 2-Benzyloxymethyl-7,7-diethyl-9,9-dimethyl-8-[1-(4-oxiranylmethoxy-phenyl)-ethoxy]-1,4-dioxa-8-aza-spiro[4.5]decane

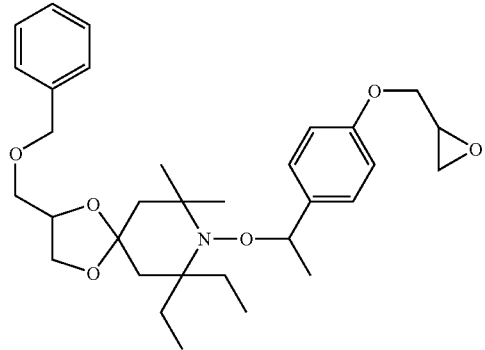

25.) Octanedioic acid bis-{7,7-diethyl-9,9-dimethyl-8-[1-(4-oxiranylmethoxy-phenyl)-ethoxy]-1,4-dioxa-8-aza-spiro[4.5]dec-2-ylmethyl} ester

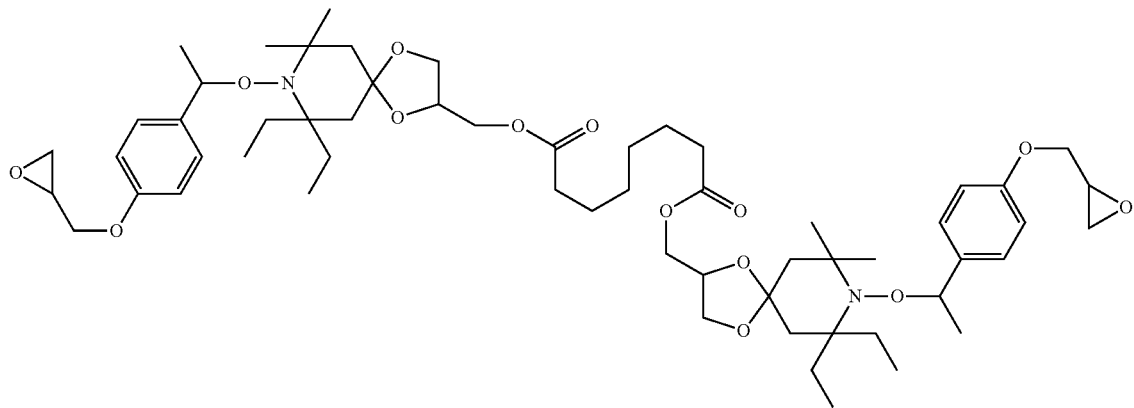

26.) Terephthalic acid bis-{7,7-diethyl-9,9-dimethyl-8-[1-(4-oxiranylmethoxy-phenyl)-ethoxy]-1,4-dioxa-8-aza-spiro[4.5]dec-2-ylmethyl} ester

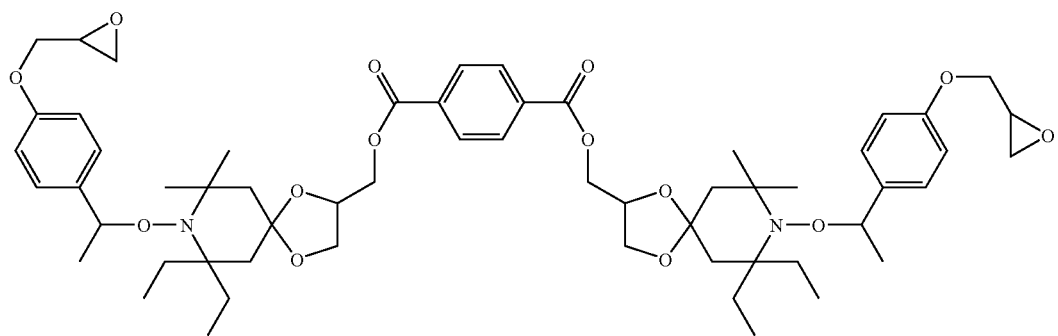

27.) 1',4'-Bis-{7,7-diethyl-9,9-dimethyl-8-[1-(4-oxiranylmethoxy-phenyl)-ethoxy]-1,4-dioxa-8-aza-spiro[4.5]dec-2-ylmethyl}-oxybutane

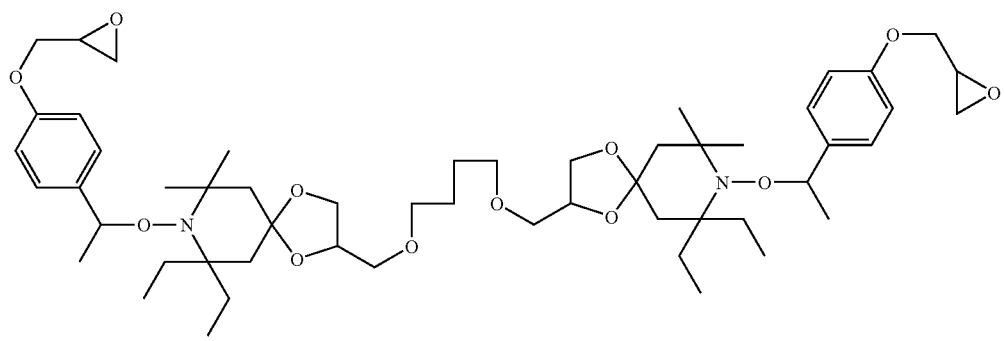

TABLE 2-continued

28.) 7,7-Diethyl-2,2,9,9-tetramethyl-8-[1-(4-oxiranylmethoxy-phenyl)-ethoxy]-1,4-dioxa-8-aza-spiro[4.5]decane

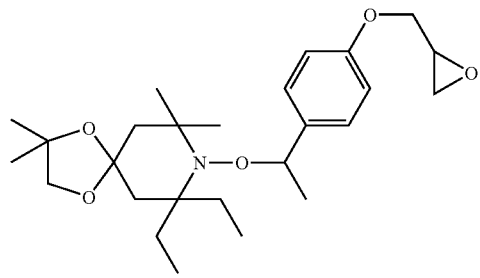

29.) 7,7-Diethyl-2,3,9,9-tetramethyl-8-[1-(4-oxiranylmethoxy-phenyl)-ethoxy]-1,4-dioxa-8-aza-spiro[4.5]decane

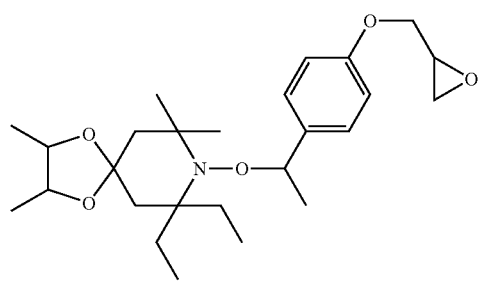

30.) 4,4-(o-Phenylendioxy)-2,2-diethyl-6,6-dimethyl-1-[1'-(4'-oxiranylmethoxy-phenyl)-ethoxy]-piperidine

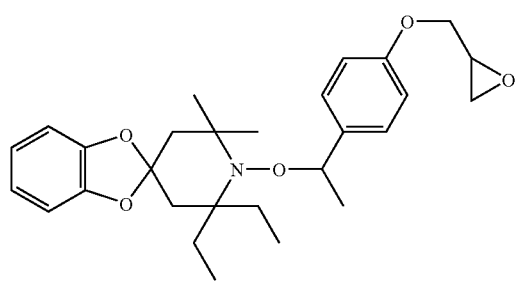

31.) 4,4-(1',2'-cyclohexylendioxy)-2,2-diethyl-6,6-dimethyl-1-[1''-(4''-oxiranylmethoxy-phenyl)-ethoxy]-piperidine

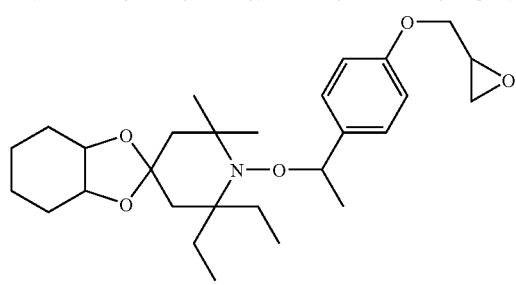

32.) 7,7-Diethyl-9,9-dimethyl-8-[1-(4-oxiranylmethoxy-phenyl)-ethoxy]-1,4-dioxa-8-aza-spiro[4.5]decane-2,3-dicarboxylic acid dimethyl ester

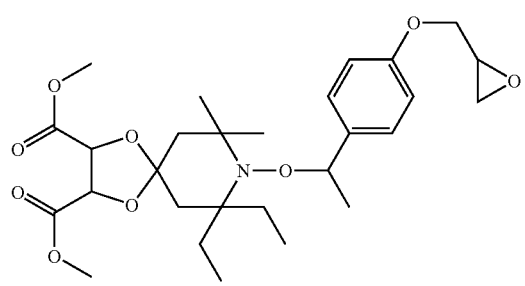

TABLE 2-continued

33.) 8,8-Diethyl-10,10-dimethyl-9-[1-(4-oxiranylmethoxy-phenyl)-ethoxy]-1,5-dioxa-9-aza-spiro[5.5]undecane

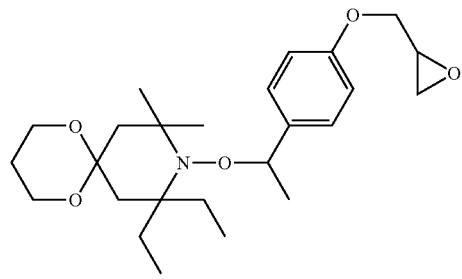

34.) 8,8-Diethyl-3,3,10,10-tetramethyl-9-[1-(4-oxiranylmethoxy-phenyl)-ethoxy]-1,5-dioxa-9-aza-spiro[5.5]undecane

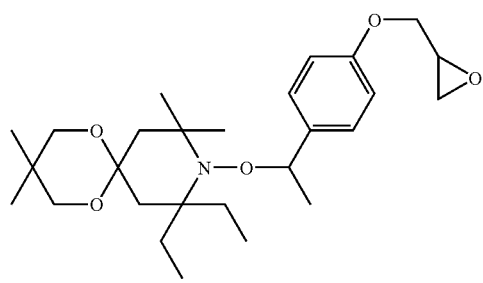

35.) 3,8,8-Triethyl-3,10,10-trimethyl-9-[1-(4-oxiranylmethoxy-phenyl)-ethoxy]-1,5-dioxa-9-aza-spiro[5.5]undecane

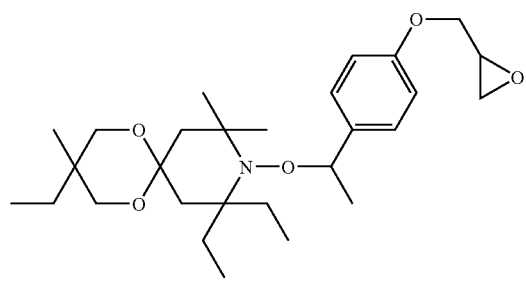

36.) 3,3,8,8-Tetraethyl-10,10-dimethyl-9-[1-(4-oxiranylmethoxy-phenyl)-ethoxy]-1,5-dioxa-9-aza-spiro[5.5]undecane

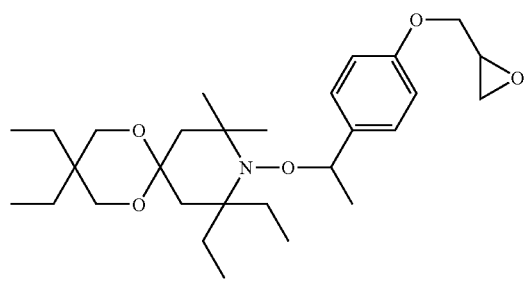

37.) 8,8-Diethyl-3,10,10-trimethyl-9-[1-(4-oxiranylmethoxy-phenyl)-ethoxy]-3-propyl-1,5-dioxa-9-aza-spiro[5.5]undecane

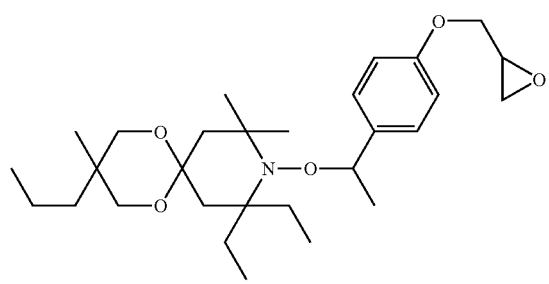

TABLE 2-continued

38.) 3-Butyl-3,8,8-triethyl-10,10-dimethyl-9-[1-(4-oxiranylmethoxy-phenyl)-ethoxy]-1,5-dioxa-9-aza-spiro[5.5]undecane

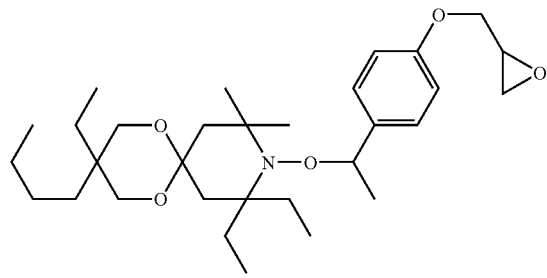

39.) 2,2-Diethyl-4,4-dimethyl-3-[1-(4-oxiranylmethoxy-phenyl)-ethoxy]-7,16-dioxa-3-aza-dispiro[5.2.5.2]hexadec-11-ene

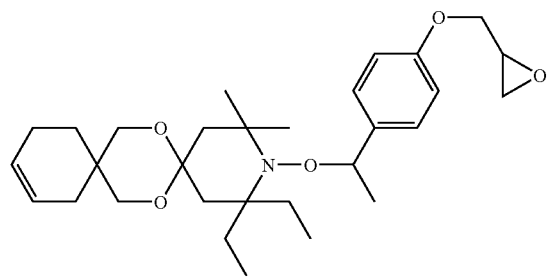

40.) {8,8-Diethyl-3,10,10-trimethyl-9-[1-(4-oxiranylmethoxy-phenyl)-ethoxy]-1,5-dioxa-9-aza-spiro[5.5]undec-3-yl}-methanol

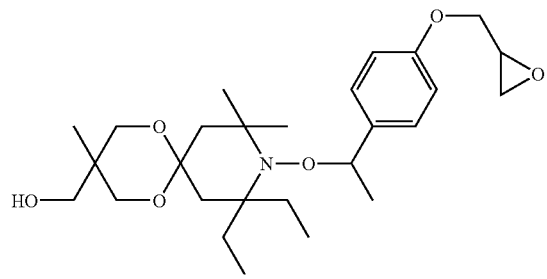

41.) {3,8,8-Triethyl-10,10-dimethyl-9-[1-(4-oxiranylmethoxy-phenyl)-ethoxy]-1,5-dioxa-9-aza-spiro[5.5]undec-3-yl}-methanol

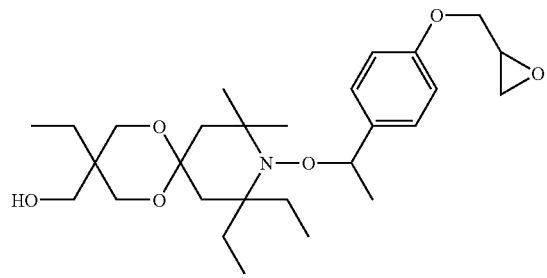

42.) 8,8-Diethyl-3-methoxymethyl-3,10,10-trimethyl-9-[1-(4-oxiranylmethoxy-phenyl)-ethoxy]-1,5-dioxa-9-aza-spiro[5.5]undecane

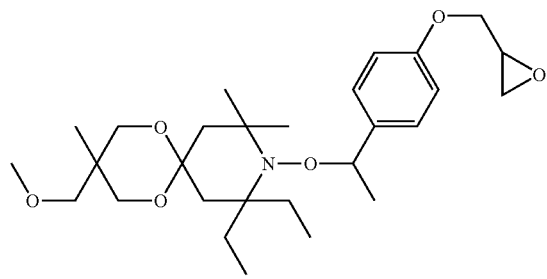

TABLE 2-continued

43.) 3-Cyclohexyloxymethyl-8,8-diethyl-3,10,10-trimethyl-9-[1-(4-oxiranylmethoxy-phenyl)-ethoxy]-1,5-dioxa-9-aza-spiro[5.5]undecane

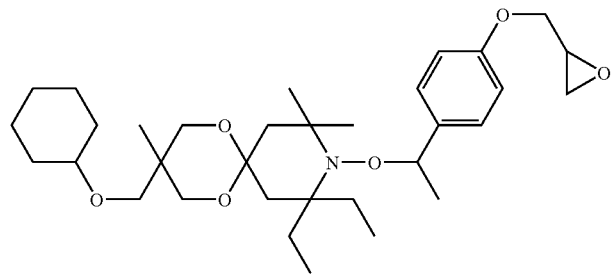

44.) 3-Benzyloxymethyl-8,8-diethyl-3,10,10-trimethyl-9-[1-(4-oxiranylmethoxy-phenyl)-ethoxy]-1,5-dioxa-9-aza-spiro[5.5]undecane

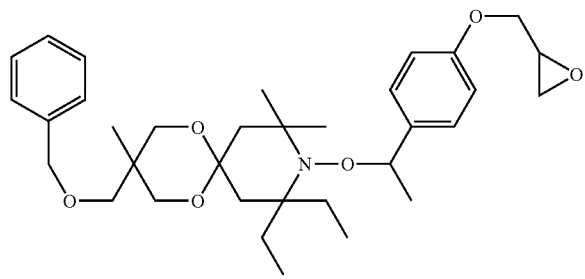

45.) Acetic acid 8,8-diethyl-3,10,10-trimethyl-9-[1-(4-oxiranylmethoxy-phenyl)-ethoxy]-1,5-dioxa-9-aza-spiro[5.5]undec-3-ylmethyl ester

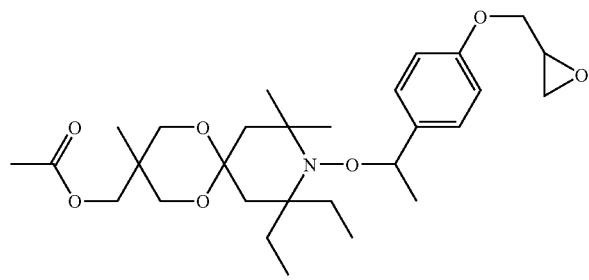

46.) Octanedioic acid bis-{8,8-diethyl-3,10,10-trimethyl-9-[1-(4-oxiranylmethoxy-phenyl)-ethoxy]-1,5-dioxa-9-aza-spiro[5.5]undec-3-ylmethyl} ester

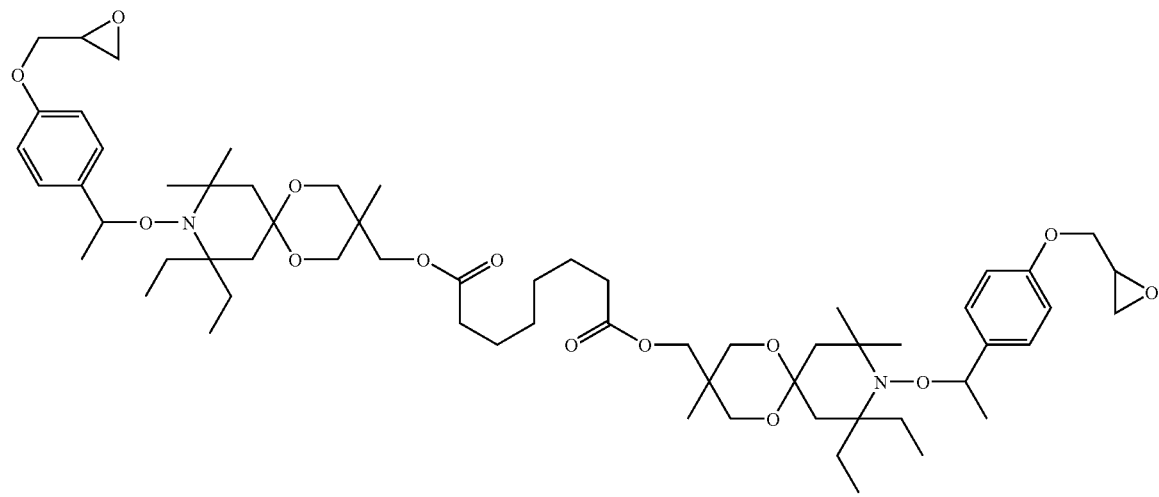

47.) 1',6'-Bis-{3,8,8-triethyl-10,10-dimethyl-9-[1-(4-oxiranylmethoxy-phenyl)-ethoxy]-1,5-dioxa-9-aza-spiro[5.5]undec-3-ylmethyl}-oxyhexane

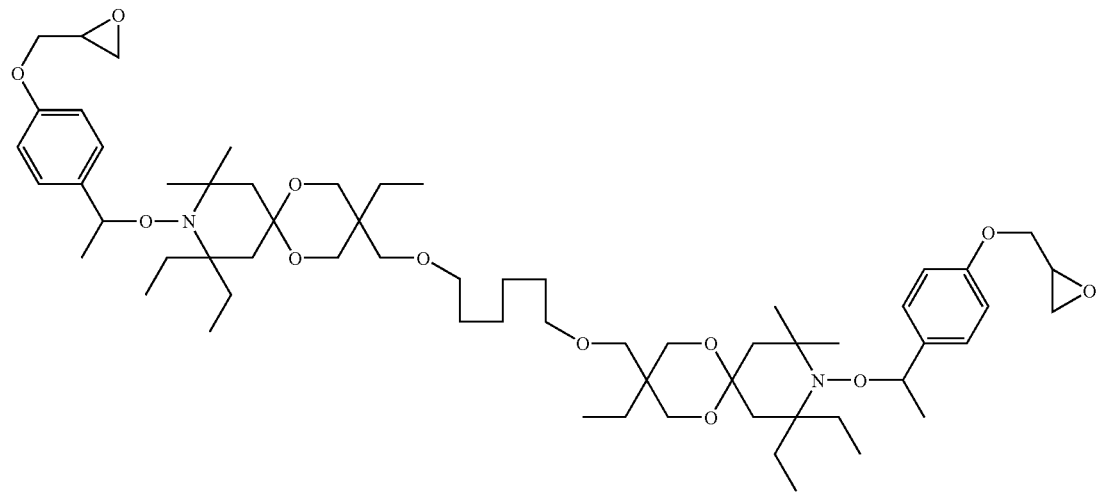

48.) 8,8-Diethyl-3,10,10-trimethyl-9-[1-(4-oxiranylmethoxy-phenyl)-ethoxy]-1,5-dioxa-9-aza-spiro[5.5]undecane-3-carboxylic acid methyl ester

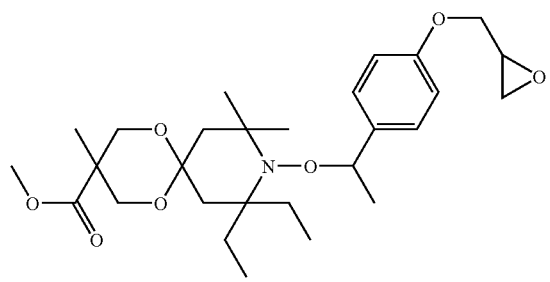

49.) 8,8-Diethyl-10,10-dimethyl-9-[1-(4-oxiranylmethoxy-phenyl)-ethoxy]-1,5-dioxa-9-aza-spiro[5.5]undecane-3,3-dicarboxylic acid diethyl ester

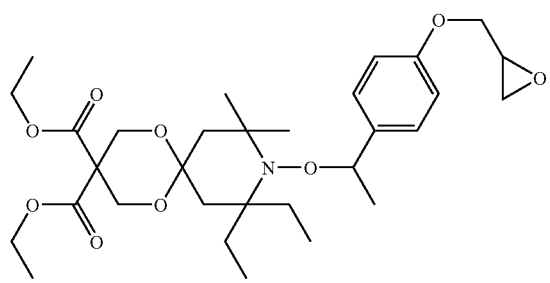

50.) 3,3-Bis-{8,8-diethyl-10,10-dimethyl-9-[1-(4-oxiranylmethoxy-phenyl)-ethoxy]-1,5-dioxa-9-aza}-spiro[5.5]undecane

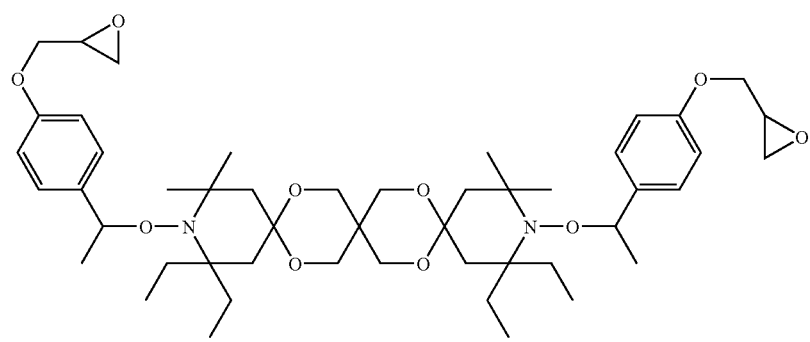

TABLE 2-continued

51.) 2,2-Diethyl-4,4-dimethyl-3-[1-(4-oxiranylmethoxy-phenyl)-ethoxy]-7,12-dioxa-3-aza-spiro[5.6]dodec-9-ene

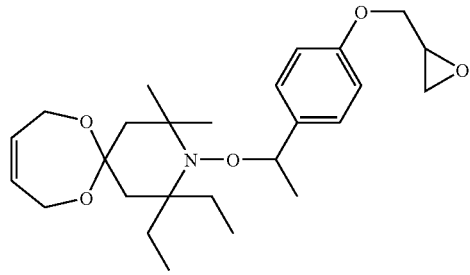

TABLE 3

1.) 4,4-Dimethoxy-2,2,6,6-tetramethyl-1-[1-(4-oxiranylmethoxy-phenyl)-ethoxy]-piperidine

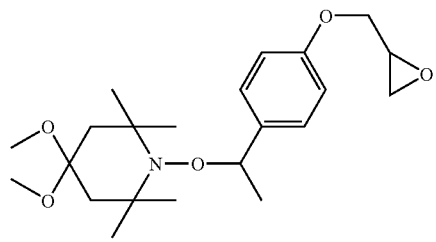

2.) 4,4-Diethoxy-2,2,6,6-tetramethyl-1-[1-(4-oxiranylmethoxy-phenyl)-ethoxy]-piperidine

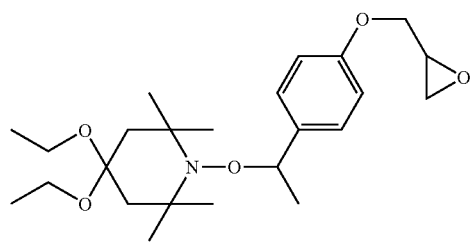

3.) 2,2,6,6-Tetramethyl-1-[1-(4-oxiranylmethoxy-phenyl)-ethoxy]-4,4-dipropoxy-piperidine

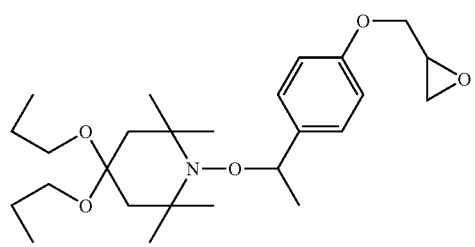

4.) 4,4-Dibutoxy-2,2,6,6-tetramethyl-1-[1-(4-oxiranylmethoxy-phenyl)-ethoxy]-piperidine

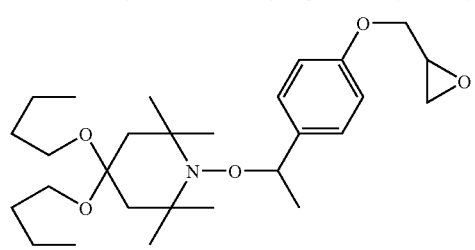

TABLE 3-continued

5.) 4,4-Diisobutoxy-2,2,6,6-tetramethyl-1-[1-(4-oxiranylmethoxy-phenyl)-ethoxy]-piperidine

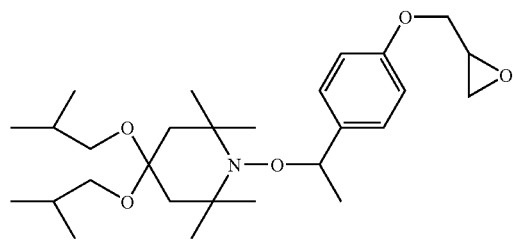

6.) 2,2,6,6-Tetramethyl-4,4-bis-octyloxy-1-[1-(4-oxiranylmethoxy-phenyl)-ethoxy]-piperidine

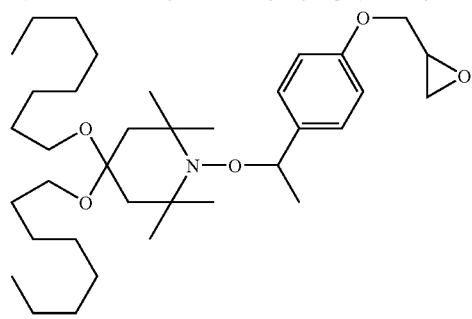

7.) 4,4-Bis-allyloxy-2,2,6,6-tetramethyl-1-[1-(4-oxiranylmethoxy-phenyl)-ethoxy]-piperidine

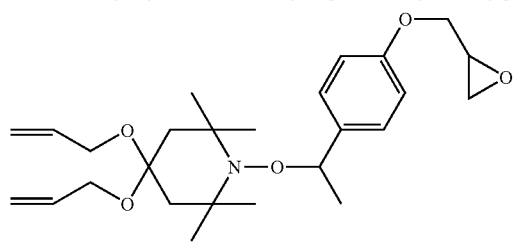

8.) 4,4-Bis-cyclohexyloxy-2,2,6,6-tetramethyl-1-[1-(4-oxiranylmethoxy-phenyl)-ethoxy]-piperidine

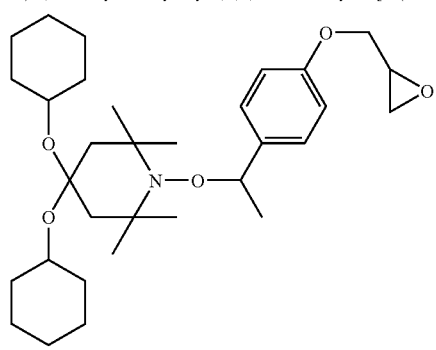

9.) 4,4-Bis-benzyloxy-2,2,6,6-tetramethyl-1-[1-(4-oxiranylmethoxy-phenyl)-ethoxy]-piperidine

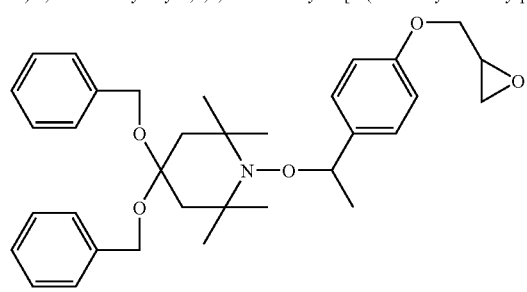

TABLE 3-continued

10.) 7,7,9,9-Tetramethyl-8-[1-(4-oxiranylmethoxy-phenyl)-ethoxy]-1,4-dioxa-8-aza-spiro[4.5]decane

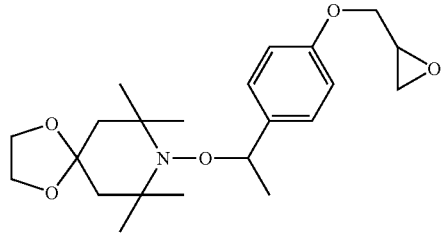

11.) 2,7,7,9,9-Pentamethyl-8-[1-(4-oxiranylmethoxy-phenyl)-ethoxy]-1,4-dioxa-8-aza-spiro[4.5]decane

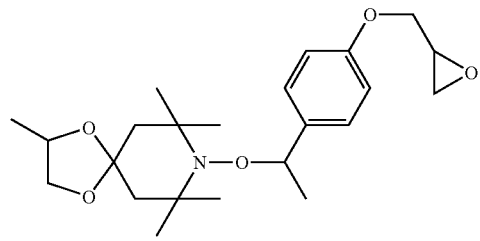

12.) 2-Ethyl-7,7,9,9-tetramethyl-8-[1-(4-oxiranylmethoxy-phenyl)-ethoxy]-1,4-dioxa-8-aza-spiro[4.5]decane

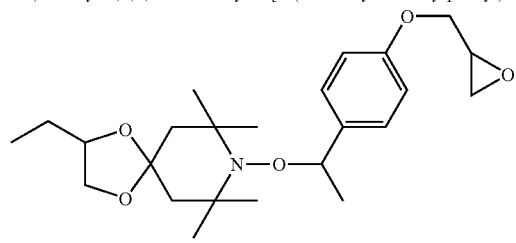

13.) 7,7,9,9-Tetramethyl-8-[1-(4-oxiranylmethoxy-phenyl)-ethoxy]-2-propyl-1,4-dioxa-8-aza-spiro[4.5]decane

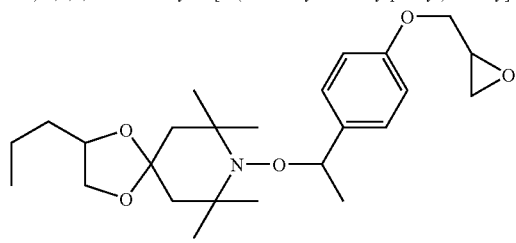

14.) 2-Butyl-7,7,9,9-tetramethyl-8-[1-(4-oxiranylmethoxy-phenyl)-ethoxy]-1,4-dioxa-8-aza-spiro[4.5]decane

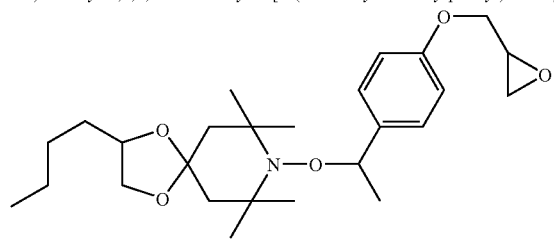

15.) 7,7,9,9-Tetramethyl-2-octyl-8-[1-(4-oxiranylmethoxy-phenyl)-ethoxy]-1,4-dioxa-8-aza-spiro[4.5]decane

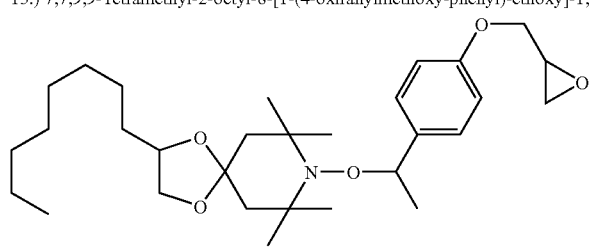

TABLE 3-continued
16.) 2-Decyl-7,7,9,9-tetramethyl-8-[1-(4-oxiranylmethoxy-phenyl)-ethoxy]-1,4-dioxa-8-aza-spiro[4.5]decane
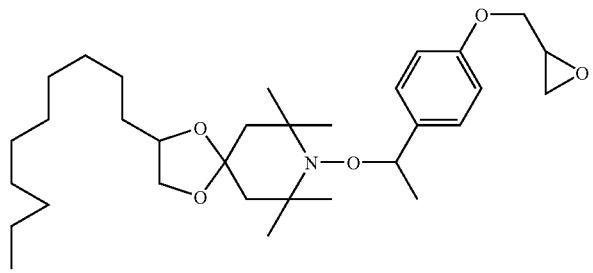
17.) 2-Dodecyl-7,7,9,9-tetramethyl-8-[1-(4-oxiranylmethoxy-phenyl)-ethoxy]-1,4-dioxa-8-aza-spiro[4.5]decane
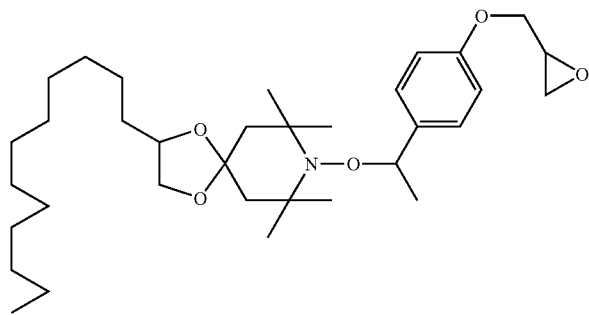
18.) {7,7,9,9-Tetramethyl-8-[1-(4-oxiranylmethoxy-phenyl)-ethoxy]-1,4-dioxa-8-aza-spiro[4.5]dec-2-yl}-methanol
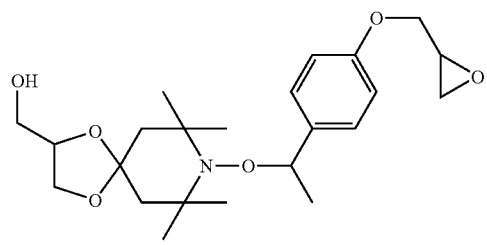
19.) Acetic acid 7,7,9,9-tetramethyl-8-[1-(4-oxiranylmethoxy-phenyl)-ethoxy]-1,4-dioxa-8-aza-spiro[4.5]dec-2-ylmethyl ester
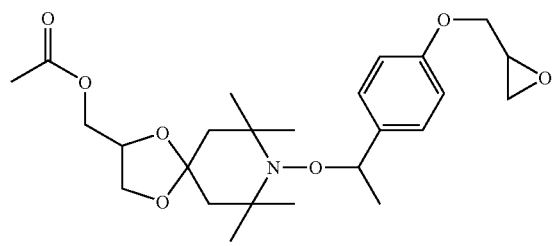

TABLE 3-continued

20.) Octadecanoic acid 7,7,9,9-tetramethyl-8-[1-(4-oxiranylmethoxy-phenyl)-ethoxy]-1,4-dioxa-8-aza-spiro[4.5]dec-2-ylmethyl ester

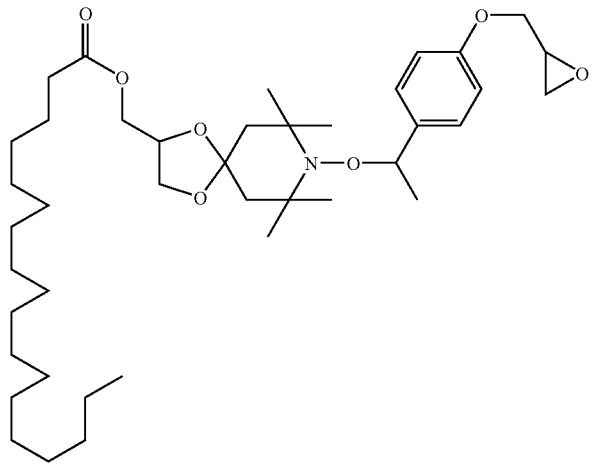

21.) Benzoic acid 7,7,9,9-tetramethyl-8-[1-(4-oxiranylmethoxy-phenyl)-ethoxy]-1,4-dioxa-8-aza-spiro[4.5]dec-2-ylmethyl ester

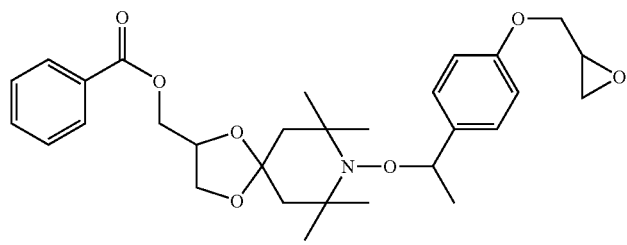

22.) 2-Methoxymethyl-7,7,9,9-tetramethyl-8-[1-(4-oxiranylmethoxy-phenyl)-ethoxy]-1,4-dioxa-8-aza-spiro[4.5]decane

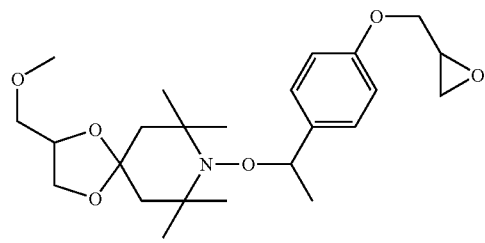

23.) 2-Cyclohexyloxymethyl-7,7,9,9-tetramethyl-8-[1-(4-oxiranylmethoxy-phenyl)-ethoxy]-1,4-dioxa-8-aza-spiro[4.5]decane

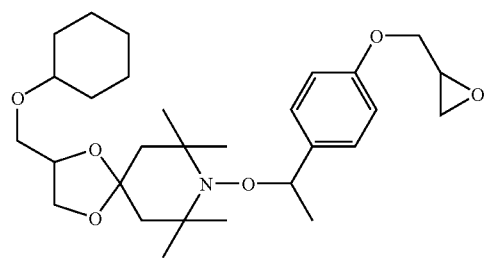

TABLE 3-continued

24.) 2-Benzyloxymethyl-7,7,9,9-tetramethyl-8-[1-(4-oxiranylmethoxy-phenyl)-ethoxy]-1,4-dioxa-8-aza-spiro[4.5]decane

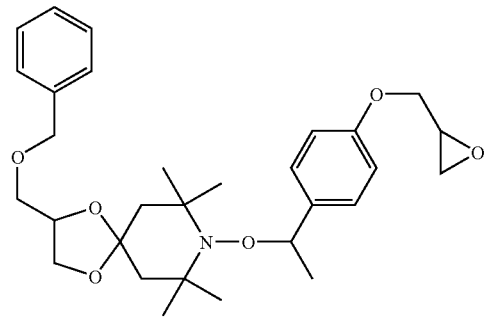

25.) Octanedioic acid bis-{7,7,9,9-tetramethyl-8-[1-(4-oxiranylmethoxy-phenyl)-ethoxy]-1,4-dioxa-8-aza-spiro[4.5]dec-2-ylmethyl} ester

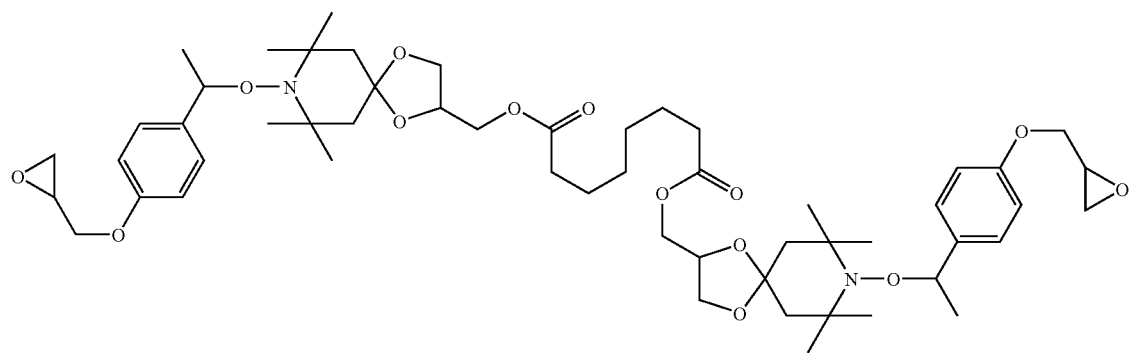

26.) Terephthalic acid bis-{7,7,9,9-tetramethyl-8-[1-(4-oxiranylmethoxy-phenyl)-ethoxy]-1,4-dioxa-8-aza-spiro[4.5]dec-2-ylmethyl} ester

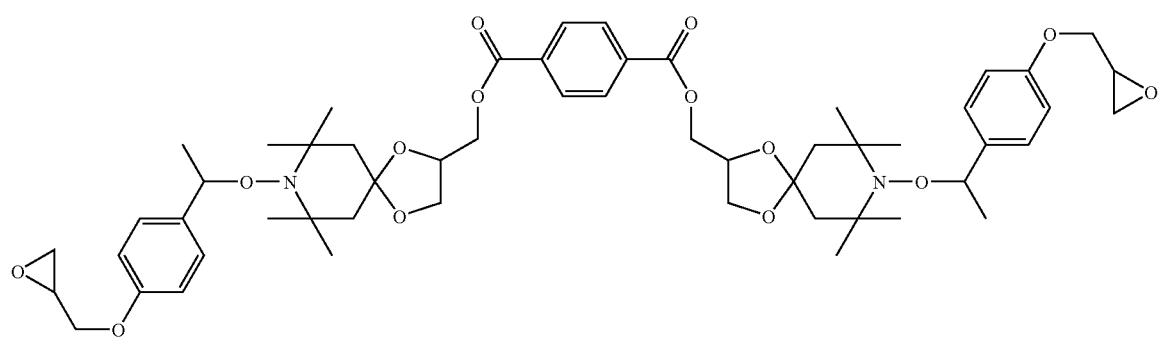

27.) 1',4'-Bis-{7,7,9,9-tetramethyl-8-[1-(4-oxiranylmethoxy-phenyl)-ethoxy]-1,4-dioxa-8-aza-spiro[4.5]dec-2-ylmethyl}-oxybutane

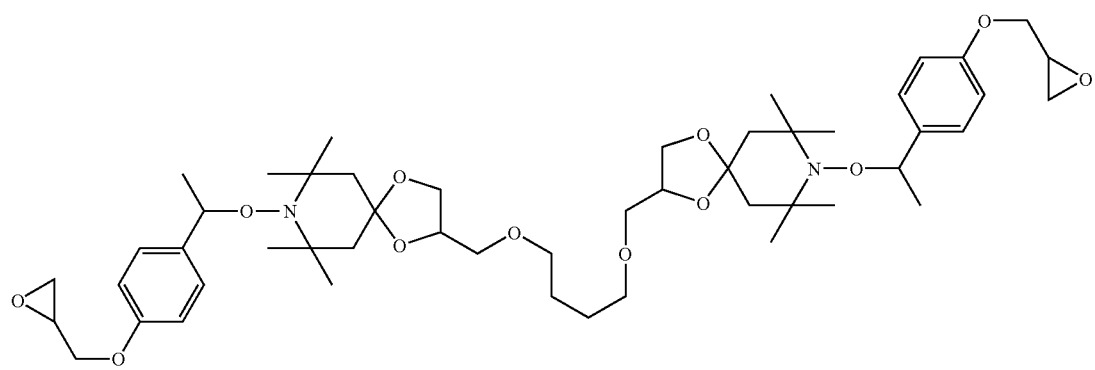

TABLE 3-continued

28.) 2,2,7,7,9,9-Hexamethyl-8-[1-(4-oxiranylmethoxy-phenyl)-ethoxy]-1,4-dioxa-8-aza-spiro[4.5]decane

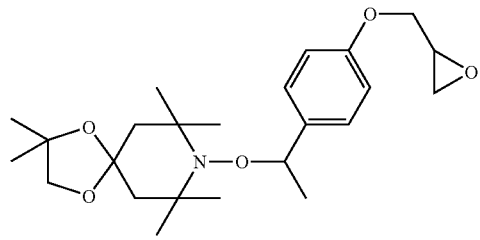

29.) 2,3,7,7,9,9-Hexamethyl-8-[1-(4-oxiranylmethoxy-phenyl)-ethoxy]-1,4-dioxa-8-aza-spiro[4.5]decane

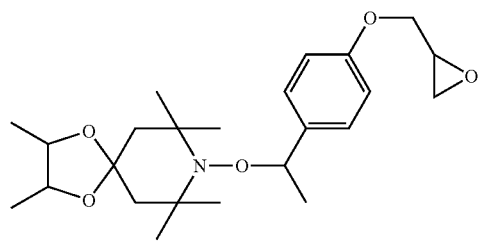

30.) 4,4-(o-Phenylendioxy)-2,2,6,6-tetramethyl-1-[1'-(4'-oxiranylmethoxy-phenyl)-ethoxy]-piperidine

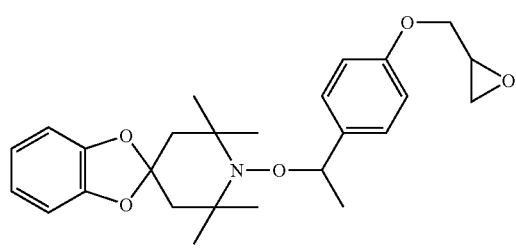

31.) 4,4-(1',2'-cyclohexylendioxy)-2,2,6,6-tetramethyl-1-[1''-(4''-oxiranylmethoxy-phenyl)-ethoxy]-piperidine

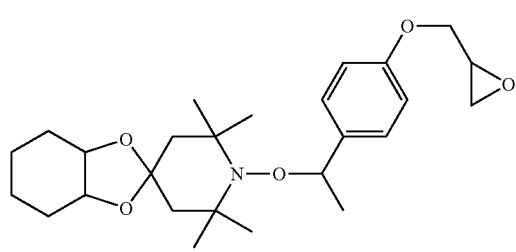

32.) 7,7,9,9-Tetramethyl-8-[1-(4-oxiranylmethoxy-phenyl)-ethoxy]-1,4-dioxa-8-aza-spiro[4.5]decane-2,3-dicarboxylic acid dimethyl ester

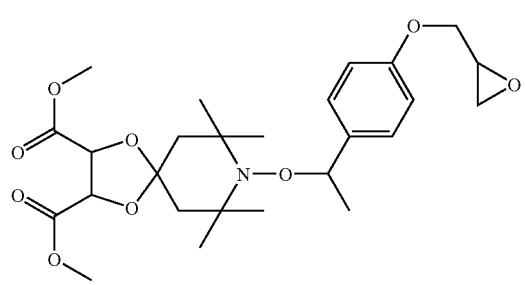

TABLE 3-continued

33.) 8,8,10,10-Tetramethyl-9-[1-(4-oxiranylmethoxy-phenyl)-ethoxy]-1,5-dioxa-9-aza-spiro[5.5]undecane

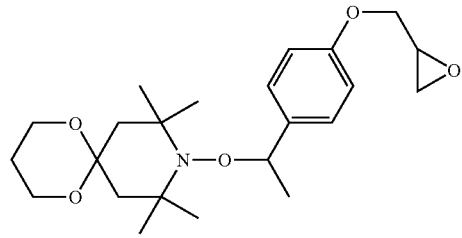

34.) 3,3,8,8,10,10-Hexamethyl-9-[1-(4-oxiranylmethoxy-phenyl)-ethoxy]-1,5-dioxa-9-aza-spiro[5.5]undecane

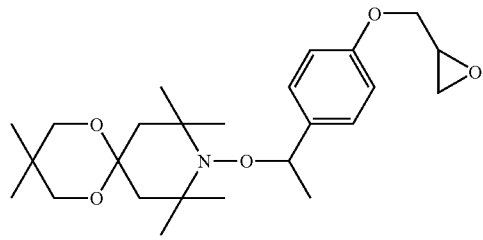

35.) 3-Ethyl-3,8,8,10,10-pentamethyl-9-[1-(4-oxiranylmethoxy-phenyl)-ethoxy]-1,5-dioxa-9-aza-spiro[5.5]undecane

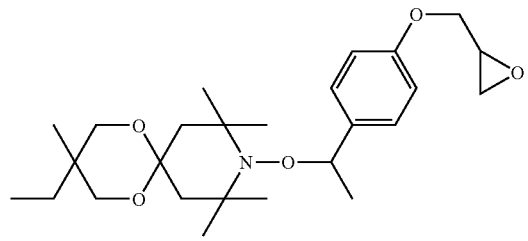

36.) 3,3-Diethyl-8,8,10,10-tetramethyl-9-[1-(4-oxiranylmethoxy-phenyl)-ethoxy]-1,5-dioxa-9-aza-spiro[5.5]undecane

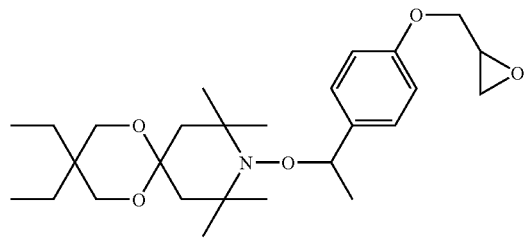

37.) 3,8,8,10,10-Pentamethyl-9-[1-(4-oxiranylmethoxy-phenyl)-ethoxy]-3-propyl-1,5-dioxa-9-aza-spiro[5.5]undecane

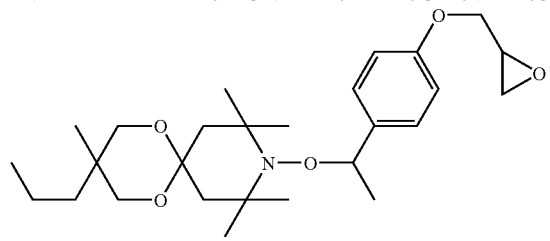

38.) 3-Butyl-3-ethyl-8,8,10,10-tetramethyl-9-[1-(4-oxiranylmethoxy-phenyl)-ethoxy]-1,5-dioxa-9-aza-spiro[5.5]undecane

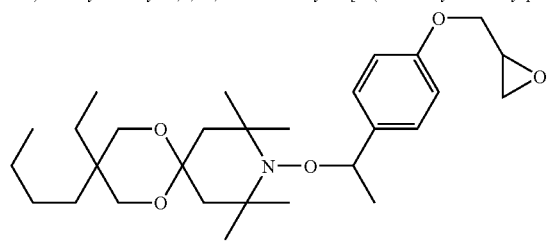

TABLE 3-continued

39.) 2,2,4,4-Tetramethyl-3-[1-(4-oxiranylmethoxy-phenyl)-ethoxy]-7,16-dioxa-3-aza-dispiro[5.2.5.2]hexadec-11-ene

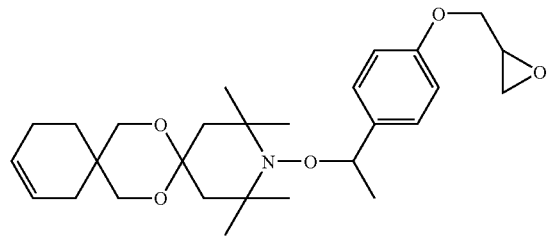

40.) {3,8,8,10,10-Pentamethyl-9-[1-(4-oxiranylmethoxy-phenyl)-ethoxy]-1,5-dioxa-9-aza-spiro[5.5]undec-3-yl}-methanol

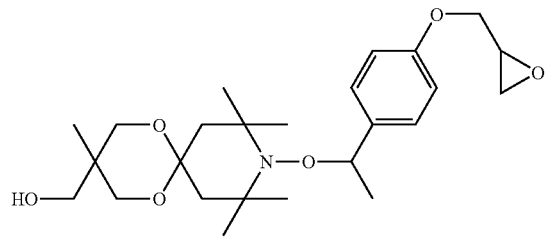

41.) {3-Ethyl-8,8,10,10-tetramethyl-9-[1-(4-oxiranylmethoxy-phenyl)-ethoxy]-1,5-dioxa-9-aza-spiro[5.5]undec-3-yl}-methanol

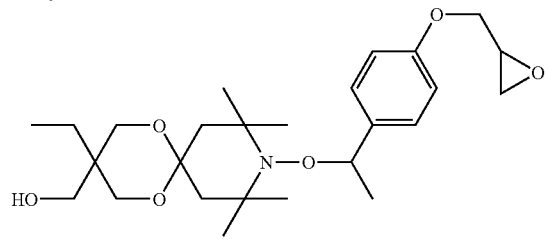

42.) 3-Methoxymethyl-3,8,8,10,10-pentamethyl-9-[1-(4-oxiranylmethoxy-phenyl)-ethoxy]-1,5-dioxa-9-aza-spiro[5.5]undecane

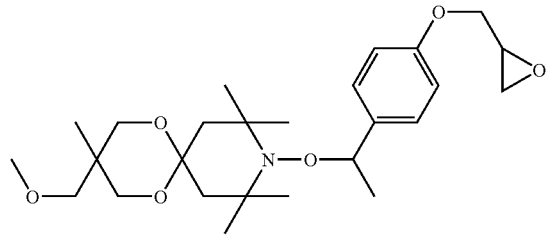

43.) 3-Cyclohexyloxymethyl-3,8,8,10,10-pentamethyl-9-[1-(4-oxiranylmethoxy-phenyl)-ethoxy]-1,5-dioxa-9-aza-spiro[5.5]undecane

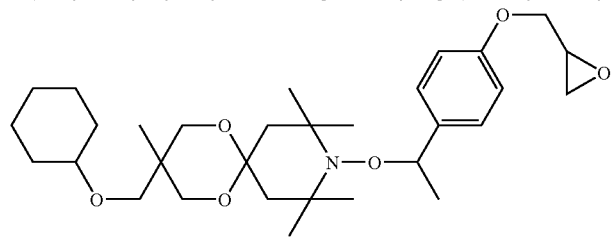

44.) 3-Benzyloxymethyl-3,8,8,10,10-pentamethyl-9-[1-(4-oxiranylmethoxy-phenyl)-ethoxy]-1,5-dioxa-9-aza-spiro[5.5]undecane

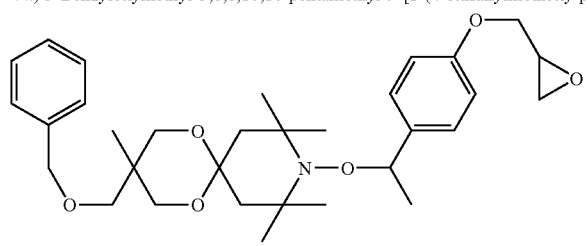

TABLE 3-continued

45.) Acetic acid 3,8,8,10,10-pentamethyl-9-[1-(4-oxiranylmethoxy-phenyl)-ethoxy]-1,5-dioxa-9-aza-spiro[5.5]undec-3-ylmethyl ester

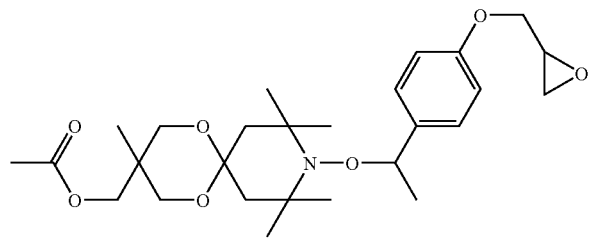

46.) Octanedioic acid bis-{3,8,8,10,10-pentamethyl-9-[1-(4-oxiranylmethoxy-phenyl)-ethoxy]-1,5-dioxa-9-aza-spiro[5.5]undec-3-ylmethyl} ester

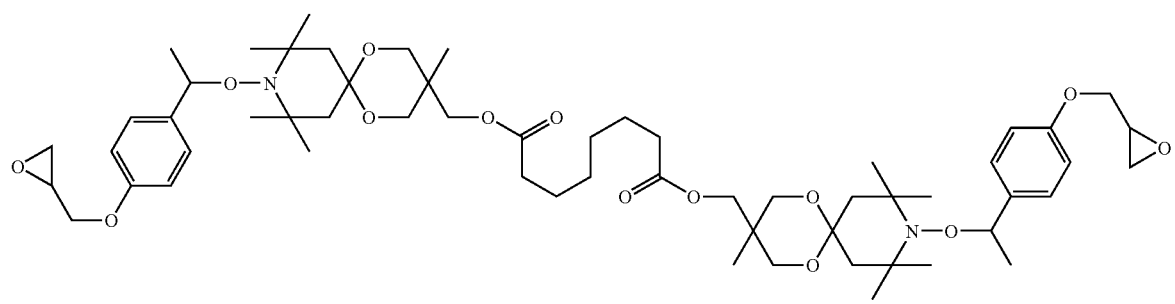

47.) 1',6'-Bis-{8,8,10,10-tetramethyl-9-[1-(4-oxiranylmethoxy-phenyl)-ethoxy]-1,5-dioxa-9-aza-spiro[5.5]undec-3-ylmethyl}-oxyhexane

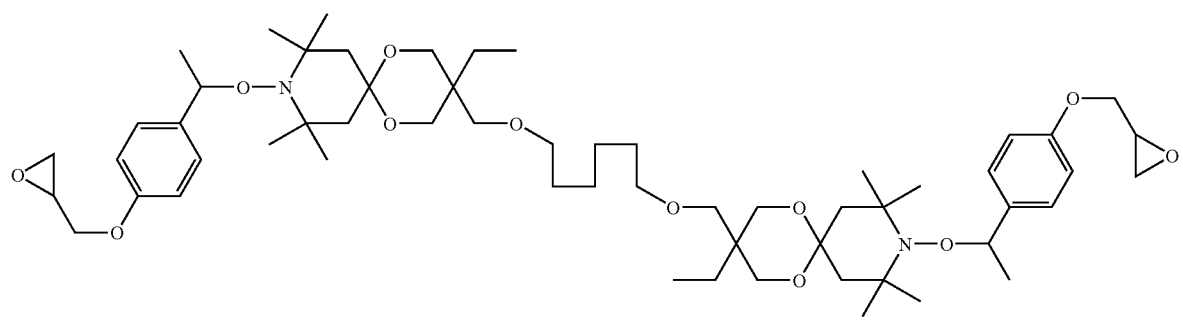

48.) 3,8,8,10,10-Pentamethyl-9-[1-(4-oxiranylmethoxy-phenyl)-ethoxy]-1,5-dioxa-9-aza-spiro[5.5]undecane-3-carboxylic acid methyl ester

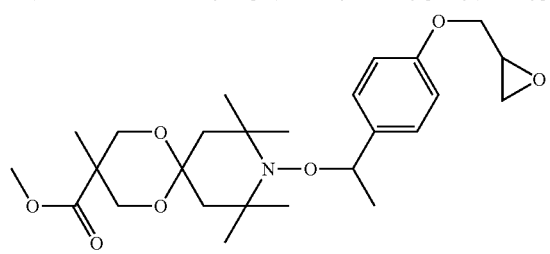

49.) 8,8,10,10-Tetramethyl-9-[1-(4-oxiranylmethoxy-phenyl)-ethoxy]-1,5-dioxa-9-aza-spiro[5.5]undecane-3,3-dicarboxylic acid diethyl ester

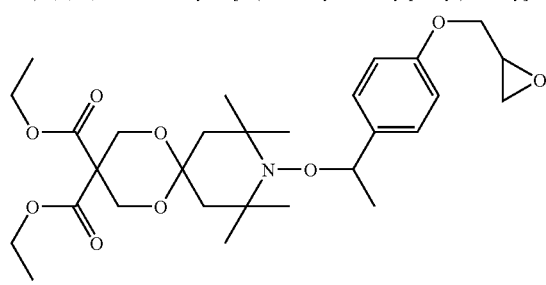

TABLE 3-continued

50.) 3,3-Bis-{8,8,10,10-tetramethyl-9-[1-(4-oxiranylmethoxy-phenyl)-ethoxy]-1,5-dioxa-9-aza}-spiro[5.5]undecane

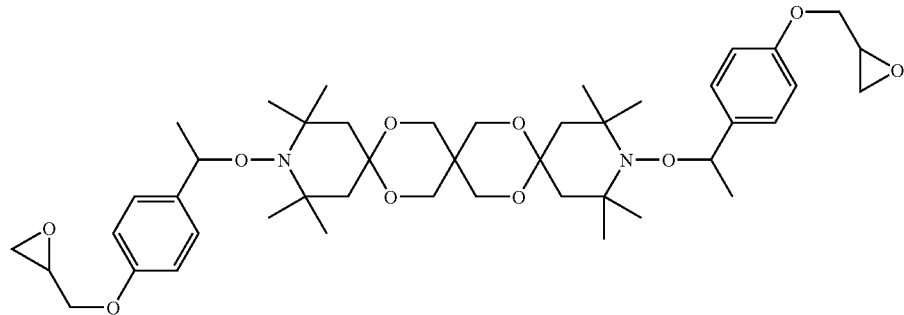

51.) 2,2,4,4-Tetramethyl-3-[1-(4-oxiranylmethoxy-phenyl)-ethoxy]-7,12-dioxa-3-aza-spiro[5.6]dodec-9-ene

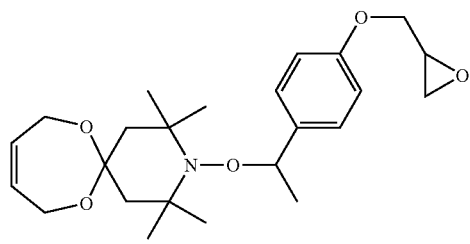

Particularly preferred are the following compounds:

4,4-Dibutoxy-2,6-diethyl-2,3,6-trimethyl-1-[1-(4-oxiranylmethoxy-phenyl)-ethoxy]-piperidine

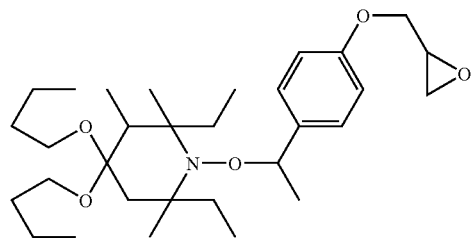

7,9-Diethyl-6,7,9-trimethyl-8-[1-(4-oxiranylmethoxy-phenyl)-ethoxy]-1,4-dioxa-8-aza-spiro[4.5]decane

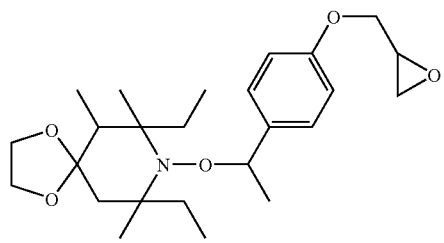

8,10-Diethyl-3,3,7,8,10-pentamethyl-9-[1-(4-oxiranylmethoxy-phenyl)-ethoxy]-1,5-dioxa-9-aza-spiro[5.5]undecane

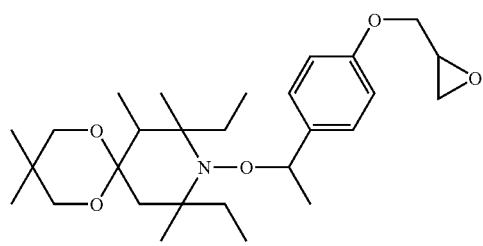

TABLE 3-continued

{8,10-Diethyl-3,7,8,10-tetramethyl-9-[1-(4-oxiranylmethoxy-phenyl)-ethoxy]-1,5-dioxa-9-aza-spiro[5.5]undec-3-yl}-methanol

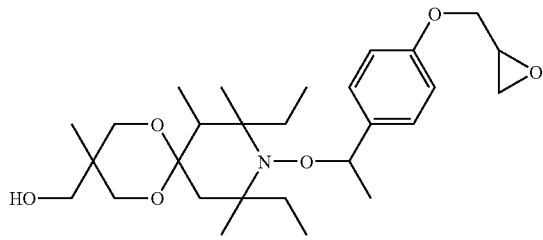

{3,8,10-Triethyl-7,8,10-trimethyl-9-[1-(4-oxiranylmethoxy-phenyl)-ethoxy]-1,5-dioxa-9-aza-spiro[5.5]undec-3-yl}-methanol

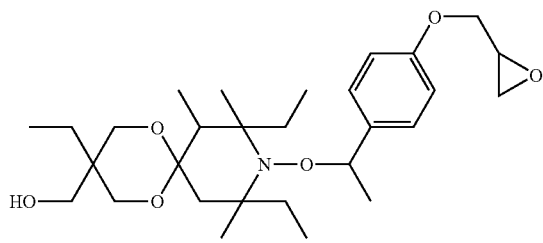

4,4-Dibutoxy-2,2-diethyl-6,6-dimethyl-1-[1-(4-oxiranylmethoxy-phenyl)-ethoxy]-piperidine

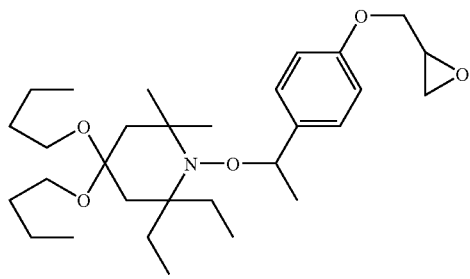

7,7-Diethyl-9,9-dimethyl-8-[1-(4-oxiranylmethoxy-phenyl)-ethoxy]-1,4-dioxa-8-aza-spiro[4.5]decane

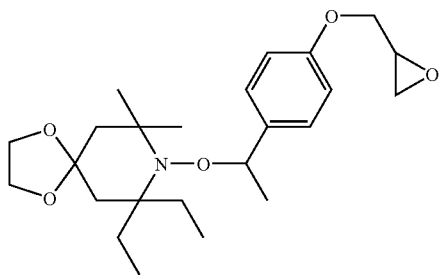

8,8-Diethyl-3,3,10,10-tetramethyl-9-[1-(4-oxiranylmethoxy-phenyl)-ethoxy]-1,5-dioxa-9-aza-spiro[5.5]undecane

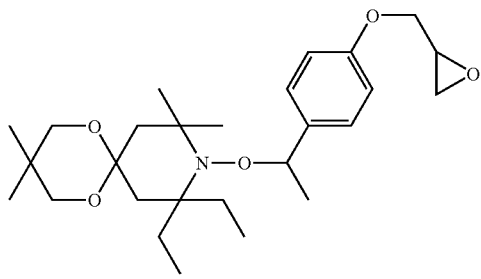

TABLE 3-continued

{8,8-Diethyl-3,10,10-trimethyl-9-[1-(4-oxiranylmethoxy-phenyl)-ethoxy]-1,5-dioxa-9-aza-spiro[5.5]undec-3-yl}-methanol

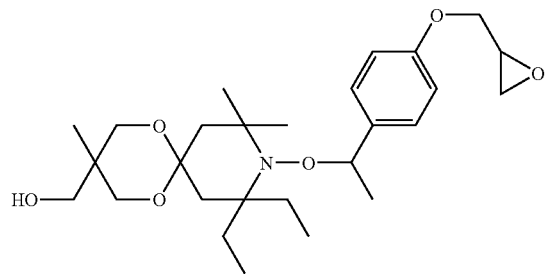

{3,8,8-Triethyl-10,10-dimethyl-9-[1-(4-oxiranylmethoxy-phenyl)-ethoxy]-1,5-dioxa-9-aza-spiro[5.5]undec-3-yl}-methanol

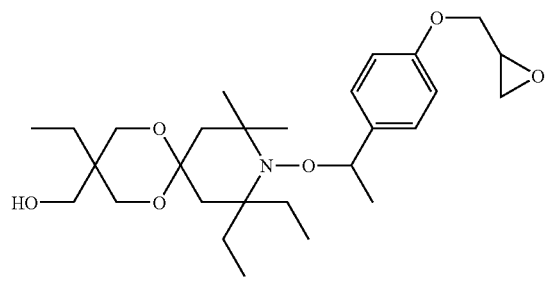

4,4-Dibutoxy-2,2,6,6-tetramethyl-1-[1-(4-oxiranylmethoxy-phenyl)-ethoxy]-piperidine

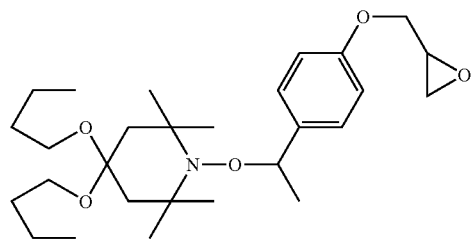

7,7,9,9-Tetramethyl-8-[1-(4-oxiranylmethoxy-phenyl)-ethoxy]-1,4-dioxa-8-aza-spiro[4.5]decane

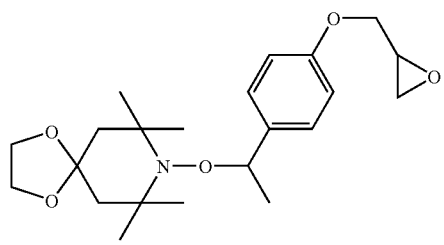

3,3,8,8,10,10-Hexamethyl-9-[1-(4-oxiranylmethoxy-phenyl)-ethoxy]-1,5-dioxa-9-aza-spiro[5.5]undecane

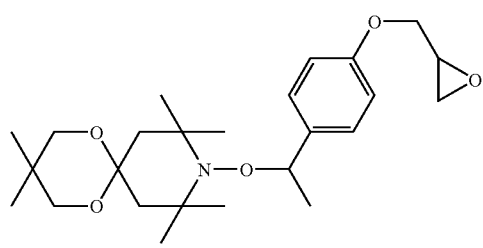

TABLE 3-continued

Most preferred is 3,3,8,8,10,10-Hexamethyl-9-[1-(4-oxiranylmethoxy-phenyl)-ethoxy]-1,5-dioxa-9-aza-spiro[5.5]undecane

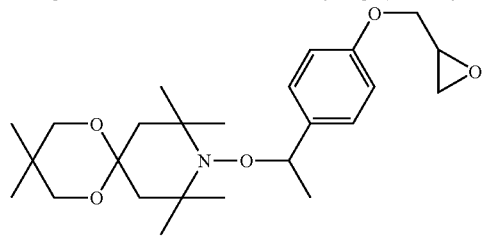

A further subject of the invention is a polymerizable composition, comprising
a) at least one ethylenically unsaturated monomer or oligomer, and
b) a compound of formula Ia, IIa or IIIa (Ia)
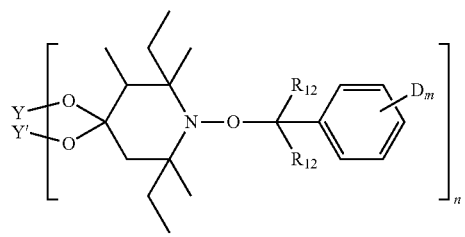

(IIa)

(IIIa)

wherein
D is a group

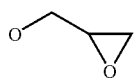

or a group C(O)—R$_{13}$;
R$_{13}$ is phenyl or C$_1$-C$_{18}$alkyl;
m is 1, 2 or 3;
n is 1 or 2;
if n is 1
Y and Y' are independently C$_1$-C$_{12}$alkyl, C$_3$-C$_{12}$alkenyl, C$_3$-C$_{12}$alkinyl, C$_5$-C$_8$cycloalkyl, phenyl, naphthyl, C$_7$-C$_9$phenylalkyl; or Y and Y' together form one of the bivalent groups —C(R$_1$)(R$_2$)—CH(R$_3$)—, CH(R$_1$)—CH$_2$—C(R$_2$)(R$_3$)—, —CH(R$_2$)—CH$_2$—C(R$_1$)(R$_3$)—, —CH$_2$—C(R$_1$)(R$_2$)—CH(R$_3$)—, o-phenylene, 1,2-cyclohexyliden, —CH$_2$—CH=CH—CH$_2$— or

;

wherein
R$_1$ is hydrogen, C$_1$-C$_{12}$alkyl, COOH, COO—(CO—C$_1$-C$_{12}$)alkyl or CH$_2$OR$_4$;
R$_2$ and R$_3$ are independently hydrogen, methyl ethyl, COOH or COO—(C$_1$-C$_{12}$)alkyl;
R$_4$ is hydrogen, C$_1$-C$_{18}$alkyl, benzyl, or a monovalent acyl residue derived from an aliphatic, cycloaliphatic or aromatic monocarboxylic acid having up to 18 carbon atoms;
if n is 2
Y and Y' together form one of the tetravalent groups

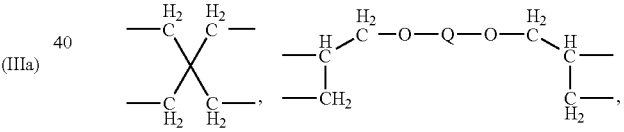

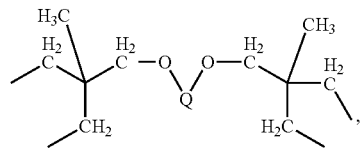

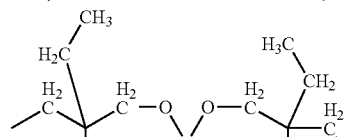

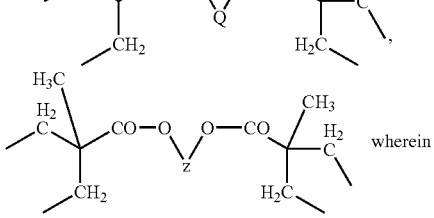

wherein

Q is a bisacyl residue which is derived from a C$_2$-C$_{12}$dicarboxylic acid or C$_1$-C$_{12}$alkylene;
Z is C$_1$-C$_{12}$alkylene;
the R$_{12}$ are independently of each other H or CH$_3$.

Definitions and preferences have already been given above for the compounds. They apply also for the composition.

The monomers suitable for use in the present invention may be water-soluble or water-insoluble. Water soluble monomers contain typically a salt of a carboxylic acid group. Water insoluble monomers are typically free of acid and phenolic groups.

Typical metal atoms are Na, K or Li.

Typical monoethylenically unsaturated monomers free of carboxylic acid and phenolic groups which are suitable for this invention include the alkyl esters of acrylic or methacrylic acids such as methyl acrylate, ethyl acrylate, butyl acrylate, methyl methacrylate, ethyl methacrylate, butyl methacrylate and isobutyl methacrylate; the hydroxyalkyl esters of acrylic or methacrylic acids, such as hydroxyethyl acrylate, hydroxypropyl acrylate, hydroxyethyl methacrylate, and hydroxypropyl methacrylate; acrylamide, methacrylamide, N-tertiary butylacrylamide, N-methylacrylamide, N,N-dimethylacrylamide; acrylonitrile, methacrylonitrile, allyl alcohol, dimethylaminoethyl acrylate, dimethylaminoethyl methacrylate, phosphoethyl methacrylate, N-vinylpyrrolidone, N-vinylformamide, N-vinylimidazole, vinyl acetate, conjugated dienes such as butadiene or isoprene, styrene, styrenesulfonic acid salts, vinylsulfonic acid salts and 2-acrylamido-2-methylpropane-sulfonic acid salts and acryloil chloride.

Preferred ethylenically unsaturated monomers or oligomers are selected from the group consisting of styrene, substituted styrene, conjugated dienes, acrolein, vinyl acetate, (alkyl)acrylic acidanhydrides, (alkyl)acrylic acid salts, (alkyl)acrylic esters or (alkyl)acrylamides.

Particularly preferred ethylenically unsaturated monomers are styrene, α-methyl styrene, p-methyl styrene, butadiene, methylacrylate, ethylacrylate, propylacrylate, n-butyl acrylate, tert.-butyl acrylate and acrylnitril.

In a most preferred composition the ethylenically unsaturated monomer is styrene.

Preferred acrylates are methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide or methacrylamide.

Examples for $C_8$-$C_{16}$ ethylenically unsaturated phenolics, which may also be used as comonomers include 4-hydroxy styrene, 4-hydroxy-α-methyl styrene, and 2,6-ditert. butyl, 4-vinyl phenol.

Another class of carboxylic acid monomers suitable for use as comonomers in this invention are the alkali metal and ammonium salts of $C_4$-$C_6$-ethylenically unsaturated dicarboxylic acids. Suitable examples include maleic acid, maleic anhydride, itaconic acid, mesaconic acid, fumaric acid and citraconic acid. Maleic anhydride (and itaconic acid are) is the preferred monoethylenically unsaturated dicarboxylic acid monomer(s).

The acid monomers suitable for use in this invention are in the form of the alkali metal salts or ammonium salts of the acid.

The polymerizable composition of the present invention may additionally comprise a solvent selected from the group consisting of water, alcohols, esters, ethers, ketones, amides, sulfoxides, hydrocarbons and halogenated hydrocarbons.

The invention also relates to a free radical polymerization process and polymers obtained thereby, which process overcomes many of the problems and disadvantages of the aforementioned prior art processes.

Preferably the initiator compound is present in an amount of from 0.01 mol-% to 20 mol-%, more preferably in an amount of from 0.01 mol-% to 10 mol-% and most preferred in an amount of from 0.05 mol-% to 10 mol-% based on the monomer or monomer mixture.

When monomer mixtures are used mol-% is calculated on the average molecular weight of the mixture.

Another subject of the present invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound of formula Ia, IIa or IIIa under reaction conditions capable of effecting scission of the O—C bond to form two free radicals, the radical

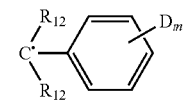

being capable of initiating polymerization.

Preferably the scission of the O—C bond is effected by heating and takes place at a temperature of between 50° C. and 160° C.

Preferred initiators and ethylenically unsaturated monomers have already been mentioned above.

Polydispersity (PD) of the polymers prepared by the present invention is preferably between 1.0 and 2.0, more preferably between 1.1 and 1.8 and most preferably between 1.1 and 1.6.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

When monomer mixtures or monomer/oligomer mixtures are used, the calculation of mol-% is based on an average molecular weight of the mixture.

Hydrophilic monomers, polymers and copolymers of the present invention can be separated from one another or from the polymerization reaction mixture by, for example, changing the pH of the reaction media and by other well known conventional separation techniques.

The polymerization temperature may range from about 50° C. to about 180° C., preferably from about 80° C. to about 150° C. At temperatures above about 180° C., the controlled conversion of the monomer into polymer decreases, and uncertain and undesirable by-products like thermally initiated polymer are formed or destruction of the polymerization regulator may occur. Frequently, these by-products discolor the polymer mixture and a purification step may be required to remove them, or they may be intractable.

Therefore high reactivity of the present initiators which are already active at relatively low temperatures leads to short reaction times. The resulting polymers are usually colourless and they can be used in most cases without any further purification step. This is an important advantage when industrial scale-up is considered.

After the polymerizing step is complete, the formed (co)polymer obtained is isolated. The isolating step of the present process is conducted by known procedures, e.g. by distilling off the unreacted monomer or by precipitation in a suitable nonsolvent, filtering the precipitated polymer followed by washing and drying the polymer.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 g/mol, preferably from 2 000 to 250 000 g/mol and, more preferably, from 2 000 to 200 000 g/mol. When produced in bulk, the number average molecular weight may be up to 500 000 (with the same minimum weights as mentioned above). The number average molecular weight may be determined by size exclusion chromatography (SEC), gel permeation chromatography (GPC), matrix assisted laser desorption/ionization mass spectrometry (MALDI-MS) or, if the initiator carries a group which can be easily distinguished from the monomer(s), by NMR spectroscopy or other conventional methods.

Thus, the present invention also encompasses in the synthesis novel block, multi-block, star, gradient, random, hyperbranched and dendritic copolymers, as well as graft or copolymers.

The polymers prepared by the present invention are useful for example in following applications:

adhesives, detergents, dispersants, emulsifiers, surfactants, defoamers, adhesion promoters, corrosion inhibitors, viscosity improvers, lubricants, rheology modifiers, impact modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerization is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)-acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623-1627, dendrimers as described by K. Matyaszewski et al. in Macromolecules 1996, Vol 29, No. 12, pages 4167-4171, graft (co)polymers as described by C. J. Hawker et al. in Macromol. Chem. Phys. 198, 155-166(1997), random copolymers as described by C. J. Hawker in Macromolecules 1996, 29, 2686-2688, or diblock and triblock copolymers as described by N. A. Listigovers in Macromolecules 1996, 29, 8992-8993.

Still further subjects of the invention are a polymer or oligomer, containing at least one initiator group

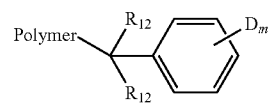

and at least one oxyamine group of formula Ib, IIb or IIIb (Ib)

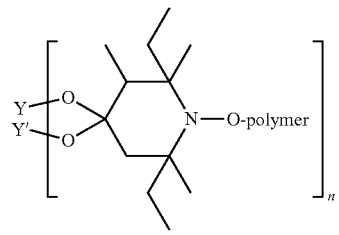

-continued

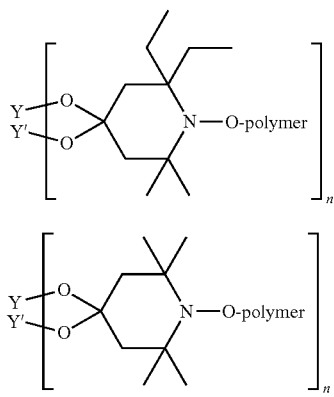
(IIb)

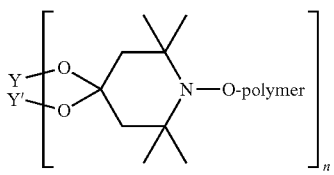
(IIIb)

wherein Y and Y' are as defined above, obtainable by the process described above; and the use of a compound of formula Ia, IIa or IIIa for polymerizing ethylenically unsaturated monomers.

Also subject of the invention is the use of a compound of formula Ia, IIa or IIIa for terminating the anionic polymerization of a diene or vinyl monomer.

When the compounds are used for such termination reactions they are usually used in an equimolar amount or in excess to the initiating base, such as for example sec. butyllithium.

The preparation of the compounds of the present invention is carried out according to known reaction steps. A general method for the preparation of the compounds of formula Ia, IIa, and IIIa starts from the 4-oxo compounds Xa or XIa which are described in GB 2335190 or from XIIa which is a known compound described for example in DE 2352127.

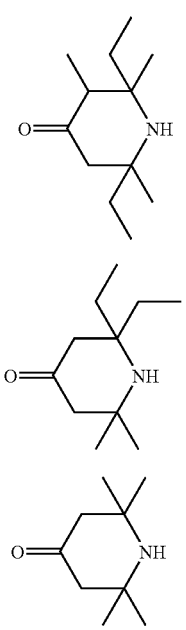

(Xa)

(XIa)

(XIIa)

These starting compounds are reacted for example with suitable monoalcohols, diols or tetrafunctional alcohols to form intermediates of formula Xb, XIb or XIIb wherein Y, Y' and n are as defined above. Such ketalization reactions are well known in the art and the corresponding compounds are mostly known. The reaction is for example described in U.S. Pat. No. 3,790,525, U.S. Pat. No. 3,899,464, U.S. Pat. No. 4,007,158 and U.S. Pat. No. 4,105,626.

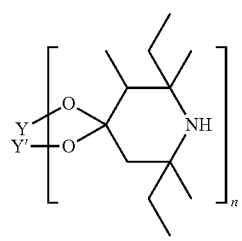
(Xb)

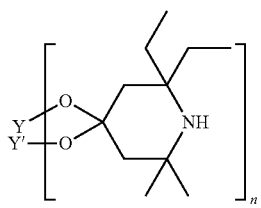
(XIb)

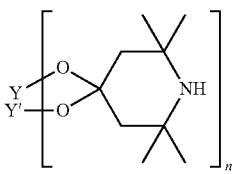
(XIIb)

The compounds of formula Xb, XIb and XIIb are oxidized according to standard procedures to the corresponding nitroxides of formula Xc, XIc and XIIc, as for example described in GB 2335190 or WO 99/46261.

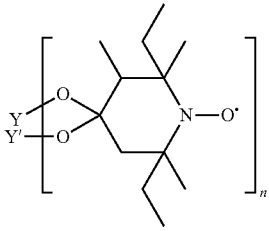
(Xc)

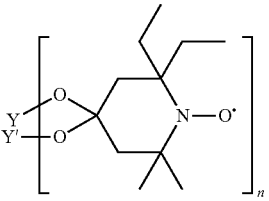
(XIc)

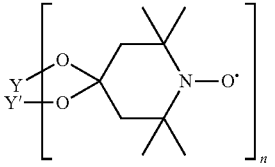
(XIIc)

The nitroxides are then reacted with a compound of formula

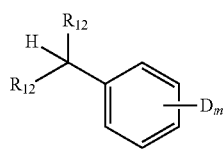

wherein $R_{12}$ and m are as defined above to obtain a compound of formula Ia, IIa or IIIa.

This coupling reaction is also described for example in GB 2335190 or in WO 99/46261.

Preferably the coupling reaction is carried out in the presence of a Cu(II) salt according to the method described in International Application No. PCT/EP01/05668.

Alternatively the nitroxides of formula Xc, XIc or XIIc can be reacted with a compound of formula

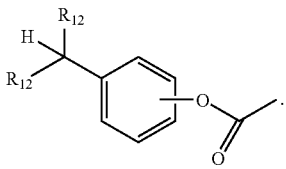

The reaction products are subsequently hydrolyzed to form a compound of formula Xd, XId or XIId.

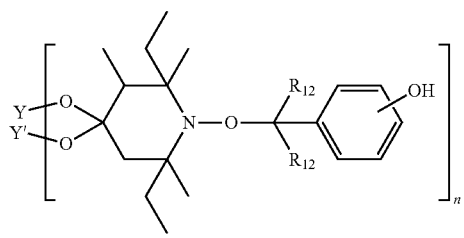
(Xd)

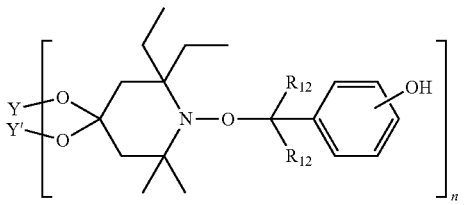
(XId)

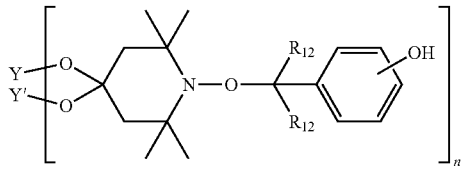
(XIId)

These compounds are novel and consequently are also subject of the present invention. The above given definitions and preferences apply also for the compounds of formula Xd, XId and XIId.

The compounds of formula Xd, XId and XIId can be reacted with epichlorohydrine and compounds according to formula Ia, IIa or IIIa are obtained.

The following examples illustrate the invention.

Preparation of an Intermediate According to Formula XIId.

Preparation of acetic acid 4-[1-(3,3,8,8,10,10-hexamethyl-1,5-dioxa-9-aza-spiro[5.5]undec-9-yloxy)-ethyl]-phenyl ester

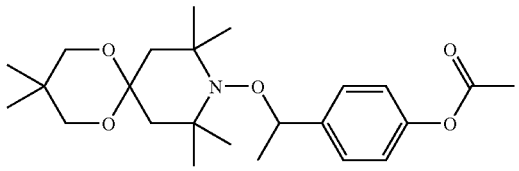

A mixture of 25.6 g 3,3,8,8,10,10-hexamethyl-1,5-dioxa-9-aza-spiro[5.5]undecan-9-oxyl (prepared according to EP 574666A1) and 82.1 g acetic acid 4-ethyl-phenyl ester are heated to 50° C. with stirring and 0.68 ml of an ethanolic solution containing 0.13 g copper(II)chloride is added. The temperature is raised to 65° C. and 19.4 g of an aqueous solution of butylhydroperoxide in water (70%) are dropwise added. The reaction mixture is allowed to further react for 22 h at 65°-70° C. and subsequently cooled to room temperature. Excess tert.-butylhydroperoxide is removed by dropwise adding 4 ml of an aqueous sodium pyrosulfite solution (20%). To the reaction mixture 50 ml acetic acid ethylester are added and the organic and aqueous phase are separated. The organic phase is washed with a saturated NaCl solution. After drying with sodium sulfate and evaporation of the solvent an oil is obtained, from which excess acetic acid 4-ethyl-phenyl ester is removed by distillation (100° C./0.025 mbar). The residue is dissolved in methanol/hexane (4/1 by volume) on heating to reflux. After cooling to 0° C. the precipitate is filtered off. After recrystallization from acetone white crystals are obtained having a melting point of 124-125° C.

Preparation of 4-[1-(3,3,8,8,10,10-Hexamethyl-1,5-dioxa-9-aza-spiro[5.5]undec-9-yloxy)-ethyl]-phenol

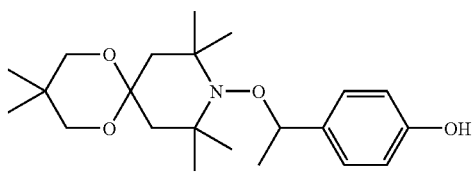

A mixture of 8 g acetic acid 4-[1-(3,3,8,8,10,10-hexamethyl-1,5-dioxa-9-aza-spiro[5.5]undec-9-yloxy)-ethyl]-phenyl ester and 3.9 g potassium carbonate in 60 ml methanol is stirred for one hour at room temperature. The mixture is cooled to 0° C. and neutralized by adding 60 ml of 0.5 M hydrochloric acid. The white suspension is diluted with water (60 ml) and filtered through a buchner funnel. The residue is washed with water and dried in a vacuum oven at 50° C. A white solid having a melting point of 133-134° C. is obtained.

Preparation of compounds according to formulae Ia, IIa and IIIa

EXAMPLE A1

Preparation of 7,7,9,9-tetramethyl-8-[1-(4-oxiranyl-methoxy-phenyl)-ethoxy]-1,4-dioxa-8-aza-spiro[4.5]decan

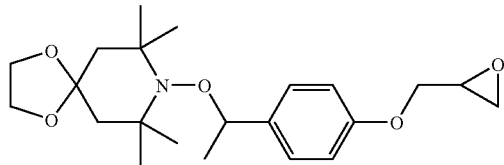

A mixture of 50 g 7,7,9,9-tetramethyl-1,4-dioxa-8-aza-spiro[4.5]decan-8-oxyl (prepared according to EP 574666A1) and 124.75 g 2-(4-ethyl-phenoxymethyl)-oxiran are heated to 60° C. with stirring and a solution of 0.32 g copper(II)chloride in 1,6 ml ethanol is added. 45 g of an aqueous solution of butylhydroperoxide in water (70%) is dropwise added. The reaction mixture is allowed to further react for 16 h at 60° C. and subsequently cooled to room temperature. Excess tert.-butylhydroperoxide is removed by dropwise adding 15 ml of an aqueous sodium pyrosulfite solution. To the reaction mixture 100 ml acetic acid ethylester are added and the organic and aqueous phase are separated. The organic phase is washed twice with 200 ml of a saturated NaCl solution. After drying with sodium sulfate and evaporation of the solvent an oil is obtained, from which excess 2-(4-ethyl-phenoxymethyl)-oxiran is removed by distillation (100° C./0.005 mbar). The residue is dissolved in hexane filtered over aluminium oxide and the solvent is again evaporated. After recrystallization from hexane white crystals are obtained having a melting point of 73.5-74.2° C.

EXAMPLE A2

Preparation of 3,3,8,8,10,10-hexamethyl-9-[1-(4-oxiranylmethoxy-phenyl)-ethoxy]-1,5-dioxa-9-aza-spiro[5.5]undecan

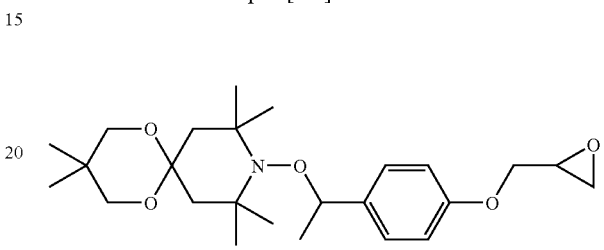

The title compound is prepared in analogy to example A1 from 3,3,8,8,10,10-hexamethyl-1,5-dioxa-9-aza-spiro[5.5]undecan-9-oxyl (prepared according to EP 574666A1). White crystals are obtained.

Elemental analysis: calculated: 69.25%; C, 9.07%; H, 3.23%; N, found: 68.86%; C, 9.05% H, 3.18%; N.

The following compounds are prepared according to example A1, starting from the corresponding nitroxide.

| No. | Struktur | Phys. Daten | NMR Data |
|---|---|---|---|
| A3 | | | $^1$H-NMR (400 MHz; δ in ppm; CDCl$_3$): 0,63 (broad s, 3H); 1,0-1,95(m, 16H); 1,45-1,47 (d, 3H); 2,73-2,75 (m, 1H); 2,88-2,9 (m, 1H); 3,2-3,55 (m, 2H); 3,85-4,3 (m, 4H); 4,72-4,77 (q, 1H); 6,84-6,87 and 7,22-7,25 (aromatic H, 4H). |
| A4 | | m.p. 52-58,5° C. | |
| A5 | | m.p. 118,5-121° C. | |

| No. | Struktur | Phys. Daten | NMR Data |
|---|---|---|---|
| A6 | 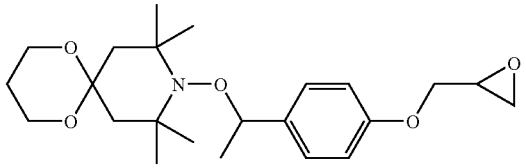 | m.p. 88,5-93° C. | |
| A7 | 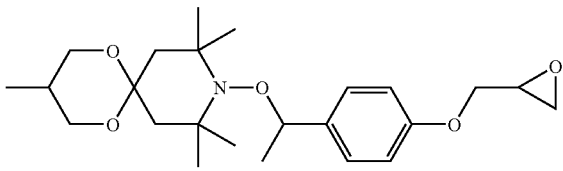 | m.p. 64,5-67° C. | |
| A8 | 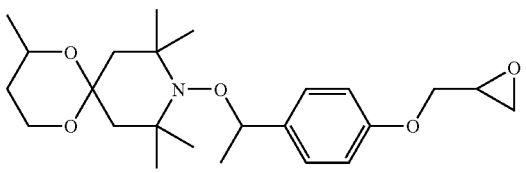 | m.p. 102-109° C. | |
| A9 | 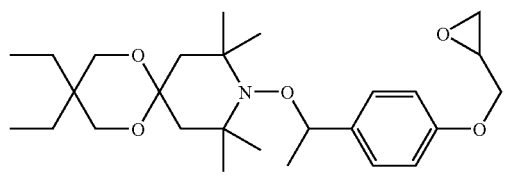 | m.p. 56-59° C. | |
| A10 | 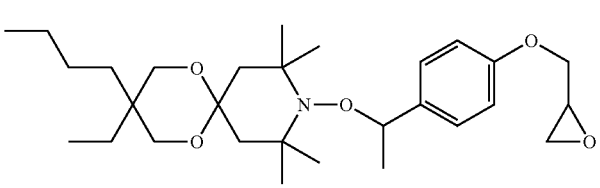 | | $^1$H-NMR (400 MHz; δ in ppm; CDCl$_3$): 0,55-1,65 (m, 31H); 1,95-2,25 (m, 2H); 2,74-2,76 (m, 1H); 2,89-2,91 (m, 1H); 3,35 (m, 1H); 3,5 (m, 4H); 3,94-3,98 (m, 1H); 4,17-4,21 (m, 1H); 4,71-4,76 (q, 1H); 6,84-6,87 and 7,22-7,25 (aromatic H, 4H). |
| A11 | 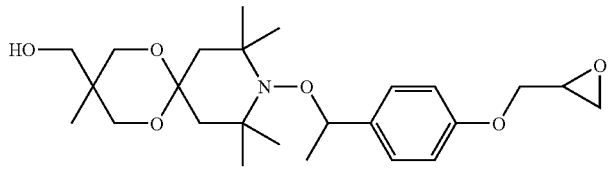 | m.p. 119,5-128° C. | |
| A12 | 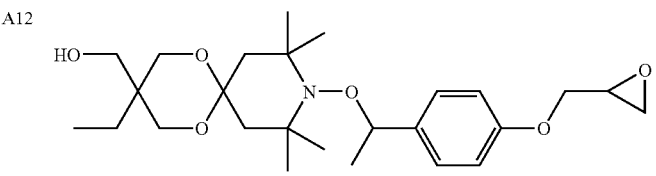 | m.p. 116-121,5° C. | |
| A13 | 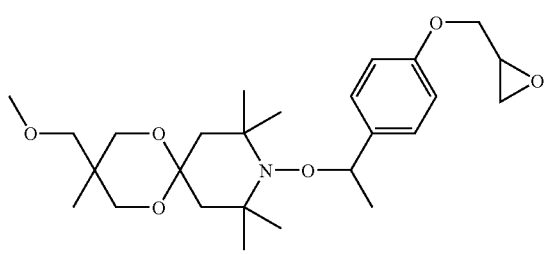 | m.p. 66,5-68,5° C. | |

-continued

| No. | Struktur | Phys. Daten | NMR Data |
|---|---|---|---|
| A14 | | m.p. 42-55° C. | |
| A15 | | | ¹H-NMR (400 MHz; δ in ppm; CDCl₃): 0,55-2,4 (m, 39H); 2,74-2,76 (m, 1H); 2,88-2,91 (m, 1H); 3,3-3,7 (m, 9H); 3,94-3,98 (m, 1H); 4,17-4,21 (m, 1H); 4,71-4,76 (q, 1H); 6,84-6,87 and 7,22-7,25 (aromatic H, 4H). |
| A16 | | m.p. 82-88° C. | ¹H-NMR (400 MHz; δ in ppm; CDCl₃): 0,6-1,65 (m, 23H); 2-2,25 (m, 2H); 2,75-2,78 (m, 1H); 2,89-2,91 (m, 1H); 3,3-3,4 (m, 1H); 3,45 (s, 4H); 3,9-4,0 (m, 1H); 4,15-4,25 (m, 1H); 4,7-4,77 (q, 1H); 6,75-7,25 (aromatic H, 4H). |
| A17 | | | ¹H-NMR (300 MHz; δ in ppm; CDCl₃): 0,7-1,7 (m, 17H); 0,95 (s, 6H); 2-2,25 (m, 2H); 2,74-2,79 (m, 1H); 2,87-2,9 (m, 1H); 3,3-3,4 (m, 1H); 3,46 (s, 4H); 3,9-4,05 (m, 1H); 4,15-4,25 (m, 1H); 5,2-5,3 (q, 1H); 6,8-7,5 (aromatic H, 4H). |

EXAMPLE A18

{4-[1-(3,3,8,8,10,10-Hexamethyl-1,5-dioxa-9-aza-spiro[5.5]undec-9-yloxy)-ethyl]-phenyl}-phenyl-methanone A mixture of 50 g 3,3,8,8,10,10-hexamethyl-1,5-dioxa-9-aza-spiro[5.5]undecan-9-oxyl (CAS 98254-32-1) and 41 g (4-Ethyl-phenyl)-phenyl-methanone (preparation by Friedel-Crafts acylation of 4-ethylbenzene with benzoylchloride) is heated to 60° C. and a solution of 0.26 g copper(II)chloride in 1.3 ml ethanol is added. 53.7 g of a 70% aqueous solution of tert-butylhydroperoxide in water are added dropwise. The reaction mixture is allowed to further react for 28 h and subsequently cooled to room temperature. Excess tert-butylhydroperoxide is then removed by dropwise adding an aqueous solution of sodium pyrosulfite. To the reaction mixture 100 ml of ethyl acetate are added and the organic phase is separated from the aqueous phase. The organic phase is washed twice with water (200 ml) and the solvent evaporated.

The residue is purified chromatographically on silica gel with hexane/ethyl acetate (7:3 by volume) as the eluente. After recrystallization from pentane/ethanol (5:3 by volume) white crystals of a compound of formula

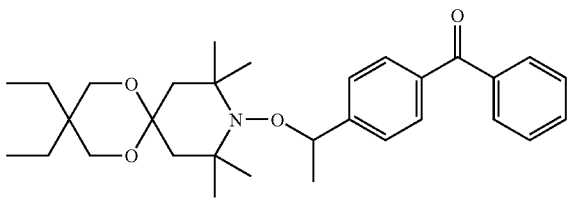

are obtained having a melting range of 104-117° C.

¹H-NMR (300 MHz; δ in ppm; CDCl₃): 0.7 (s broad, 3H); 0.94 (s broad, 6H); 1.18 (s broad, 3H); 1.33 (s broad, 6H); 1.51-1.53 (d, 3H); 1.4-1.65 (m, 2H); 2-2.25 (m, 2H); 3.46 (s broad, 4H); 4.84-4.91 (q, 1H); 7.4-7.9 (aromatic H, 9H).

EXAMPLE A19

8,8-Diethyl-3,3,10,10-tetramethyl-9-[1-(4-oxiranyl-methoxy-phenyl)-ethoxy]-1,5-dioxa-9-aza-spiro[5.5]undecane To a stirred mixture of 25.6 g 8,8-diethyl-3,3,10,10-tetramethyl-1,5-dioxa-9-aza-spiro[5.5]undecan-9-oxyl and 80.2 g 2-(4-ethyl-phenoxymethyl)-oxirane at 50° C. is added a solution of 0.12 g copper(II)chloride in 0.6 ml ethanol. The temperature of the reaction mixture is increased to 70° C. and 11.6 g of a 70% aqueous solution of tert-butylhydroperoxide in water are added dropwise. The reaction mixture is allowed to further react for 6 h at 70° C. and subsequently cooled to room temperature. Excess tert-butylhydroperoxide is removed by dropwise adding an aqueous solution of sodium pyrosulfite (2 ml). To the reaction mixture 50 ml of ethyl acetate and 50 ml 10% aqueous solution of sodium chloride are added. The mixture is filtered through celite and the organic phase is separated. The organic phase is washed three times with 10% aqueous solution of sodium chloride (100 ml) and dried over sodium sulfate. After evaporation of the solvent an oil is obtained, from which excess 2-(4-ethyl-phenoxymethyl)-oxirane is removed by distillation (80° C., 0.025 mbar). A highly viscous residue is obtained which crystallises on standing at room temperature. After recrystallization twice from methanol white crystals of the compound of formula

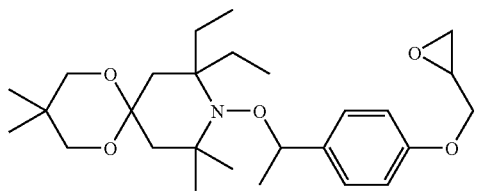

are obtained having a melting point of 82-85° C.

According to the preparation of 8,8-Diethyl-3,3,10,10-tetramethyl-9-[1-(4-oxiranylmethoxy-phenyl)-ethoxy]-1,5-dioxa-9-aza-spiro[5.5]undecane, the following compounds are synthesized in analogy:

EXAMPLE A22

8,10-diethyl-3,3,7,8,10-pentamethyl-9-[1-(4-oxiranylmethoxy-phenyl)-ethoxy]-1,5-dioxa-9-aza-spiro[5.5]undecane To a stirred mixture of 59.7 g 8,10-diethyl-3,3,7,8,10-pentamethyl-1,5-dioxa-9-aza-spiro[5.5]undecan-9-oxyl and 178.2 g 2-(4-ethyl-phenoxymethyl)-oxirane a solution of 0.27 g copper(II)chloride in 1.35 ml ethanol is added at about 60° C. Then 38.7 g of a 70% aqueous solution of tert-butylhydroperoxide in water are added dropwise. An exothermic reaction started and the temperature is kept at 70° C. The reaction mixture is allowed to further react for 24 h at 70° C. and subsequently cooled to room temperature. The reaction mixture is diluted with 100 ml of ethyl acetate. Excess tert-butylhydroperoxide is removed by dropwise adding an aqueous solution of sodium pyrosulfite (70 ml) below 20° C. The organic phase is separated, washed twice with 10% aqueous solution of sodium chloride (100 ml) and dried over sodium sulfate. After evaporation of the solvent an oil is obtained, from which excess 2-(4-ethyl-phenoxymethyl)-oxirane is removed by distillation (80° C., 0.025 mbar). A highly viscous resin is obtained which is dissolved in methanol (20 ml) and cooled to about −18° C. White crystals precipitate and are collected by filtration having a melting point of 141-147° C. The compound has the following structural formula

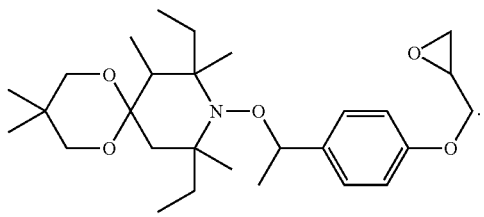

According to the preparation of 8,10-Diethyl-3,3,7,8,10-pentamethyl-9-[1-(4-oxiranylmethoxy-phenyl)-ethoxy]-1,5-dioxa-9-aza-spiro[5.5]undecane, the following compound is synthesized in analogy:

| No. | Structure | NMR-data |
| --- | --- | --- |
| A20 | 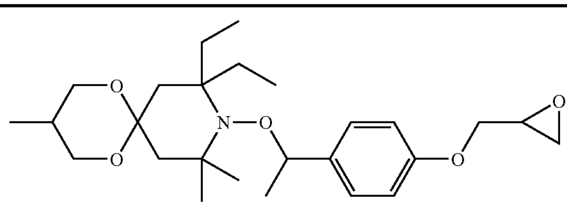 | $^1$H-NMR (400 MHz; δ in ppm; CDCl$_3$): 0,4-2,5 (m, 27H); 2,75-2,76 (m, 1H); 2,89-2,91 (m, 1H); 3,34-3,36 (m, 1H); 3,4-3,55 (m, 2H); 3,7-3,85 (m, 2H); 3,94-3,98 (m, 1H); 4,18-4,21 (m, 1H); 4,63-4,68 (q, 1H); 6,84-6,86 and 7,19-7,21 (aromatic H, 4H). |
| A21 | 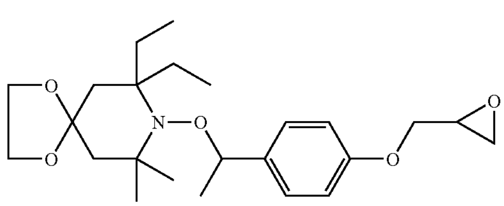 | $^1$H-NMR (400 MHz; δ in ppm; CDCl$_3$): 0,5-2,2 (m, 23 H); 2,74-2,76 (m, 1H); 2,89-2,91 (m, 1H); 3,33-3,37 (m, 1H); 3,7-4,05 (m, 5H); 4,18-4,21 (m, 1H); 4,64-4,69 (q, 1H); 6,84-6,87 and 7,19-7,21 (aromatic H, 4H). |

| No. | Structure | |
|---|---|---|
| A23 | (structure) | $^1$H-NMR (400 MHz; δ in ppm; CDCl$_3$): 0,5-2,3 (m, 25H); 2,75-2,76 (m, 1H); 2,89-2,91 (m, 1H); 3,34-3,36 (m, 1H); 3,7-4,1 (m, 5H); 4,18-4,21 (m, 1H); 4,66-4,72 (m, 1H); 6,83-6,86 and 7,18-7,21 (aromatic H, 4H). |

Polymerization Experiments with Styrene

EXAMPLE B1

Styrene is distilled under reduced pressure prior to use. In a dry, argon-purged Schlenk tube, the amounts of nitroxyl ether given in Table 1 are dissolved in 50 ml styrene. The solution is degassed in three consecutive freeze-thaw-cycles and then purged with argon. The stirred solution is then immersed in an oil bath and polymerized at the given temperature for 6 hours. After polymerization, residual monomer is removed under vacuum at 60° C. and the polymer is dried at 60° C. in vacuo until constant weight is achieved.

Molecular weight and molecular weight distributions are determined by size exclusion chromatography (SEC) on a HP 1090 liquid chromatograph (software: winGPC/Polymer Standard Services, Mainz, Germany) using THF as eluent and a column combination calibrated with narrow polystyrene standards (Polymer Laboratories). The results are given in Table 1.

Following the general description of example B1 further polymerizations in styrene were carried out and the following results obtained.

TABLE 2

NOR of example A1

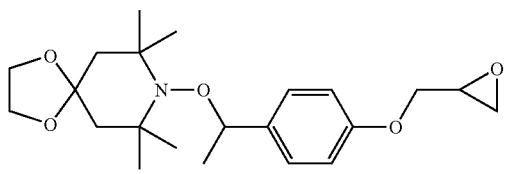

| Exp. # | Temp. (° C.) | Mol % NOR | Yield (%) | $M_n$ (calc.) | $M_n$ | $M_w$ | $M_w/M_n$ |
|---|---|---|---|---|---|---|---|
| 1 | 120 | 1 | 20 | 2400 | 1800 | 2200 | 1.25 |
| 2 | 120 | 0.1 | 41 | 43400 | 23300 | 37000 | 1.59 |
| 3 | 130 | 1 | 41 | 4700 | 3500 | 4300 | 1.23 |
| 4 | 130 | 0.1 | 55 | 58000 | 30900 | 42900 | 1.39 |

TABLE 1

NOR of example A2

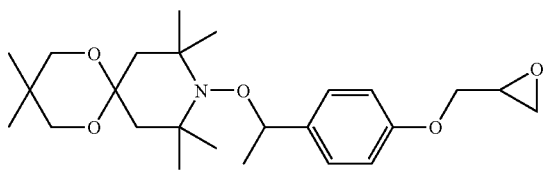

| NOR | Temp. [° C.] | mol % NOR | Styrene Conversion (%) | $M_n$ (calc.) | $M_n$ (GPC) | $M_w$ (GPC) | $M_w/M_n$ (GPC) |
|---|---|---|---|---|---|---|---|
| Example A2 | 120 | 1 mol% | 40 | 4700 | 4300 | 5200 | 1.24 |
| Example A2 | 120 | 0.1 mol% | 44 | 46000 | 28400 | 36900 | 1.30 |
| Example A2 | 130 | 1 mol% | 48 | 5300 | 4800 | 5800 | 1.21 |
| Example A2 | 130 | 0.1 mol% | 61 | 64500 | 37200 | 49500 | 1.33 |

EXAMPLE B3

TABLE 3

NOR of example A6

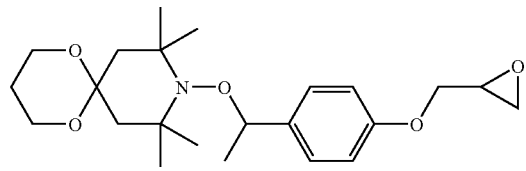

| Exp. # | Temp. (° C.) | Mol % NOR | Yield (%) | $M_n$ (calc.) | $M_n$ | $M_w$ | $M_w/M_n$ |
|---|---|---|---|---|---|---|---|
| 1 | 120 | 1 | 41 | 4600 | 3700 | 4500 | 1.22 |
| 2 | 120 | 0.1 | 46 | 47900 | 32500 | 41000 | 1.26 |
| 3 | 130 | 1 | 46 | 5200 | 3900 | 4700 | 1.18 |
| 4 | 130 | 0.1 | 61 | 63800 | 38600 | 50200 | 1.30 |

EXAMPLE B4

TABLE 4

NOR of example A5

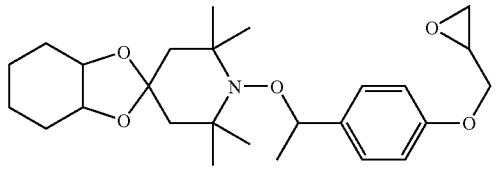

| Exp. # | Temp. (° C.) | Mol % NOR | Yield (%) | $M_n$ (calc.) | $M_n$ | $M_w$ | $M_w/M_n$ |
|---|---|---|---|---|---|---|---|
| 1 | 120 | 1 | 39 | 4500 | 3500 | 4300 | 1.21 |
| 2 | 120 | 0.1 | 51 | 53500 | 34800 | 42700 | 1.23 |
| 3 | 130 | 1 | 52 | 5800 | 4400 | 5500 | 1.24 |
| 4 | 130 | 0.1 | 59 | 61800 | 31400 | 44200 | 1.41 |

EXAMPLE B5

TABLE 5

NOR of example A4

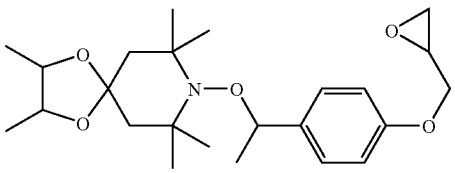

| Exp. # | Temp. (° C.) | Mol % NOR | Yield (%) | $M_n$ (calc.) | $M_n$ | $M_w$ | $M_w/M_n$ |
|---|---|---|---|---|---|---|---|
| 1 | 120 | 1 | 26 | 3100 | 2600 | 3200 | 1.23 |
| 2 | 120 | 0.1 | 37 | 39000 | 27700 | 35400 | 1.28 |
| 3 | 130 | 1 | 51 | 5700 | 4800 | 6000 | 1.24 |
| 4 | 130 | 0.1 | 57 | 59600 | 35400 | 47800 | 1.35 |

EXAMPLE B6

TABLE 6

NOR of example A9

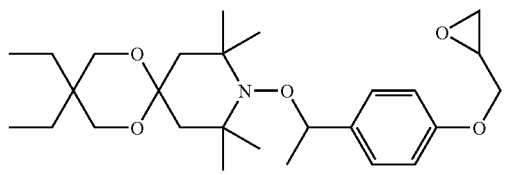

| Exp. # | Temp. (° C.) | Mol % NOR | Yield (%) | $M_n$ (calc.) | $M_n$ | $M_w$ | $M_w/M_n$ |
|---|---|---|---|---|---|---|---|
| 1 | 120 | 1 | 26 | 3100 | 2700 | 3300 | 1.26 |
| 2 | 120 | 0.1 | 38 | 40400 | 28100 | 35700 | 1.27 |
| 3 | 130 | 1 | 54 | 6100 | 5000 | 6000 | 1.20 |
| 4 | 130 | 0.1 | 60 | 62600 | 37600 | 49500 | 1.32 |

Polymerization with n-BuA

EXAMPLE B7 n-Butylacrylate is destined under reduced pressure prior to use. In a dry, argon-purged Schienk tube, the amounts of nitroxyl ether given in Table A are dissolved in 62.5 ml n-butylacrylate. The solution is degassed in three consecutive freeze-thaw-cycles and then purged with argon. The stirred solution is then immersed in an oil bath and polymerized at 130° C. for 6 hours. After polymerization, residual monomer is removed under vacuum at 30° C. and the polymer is dried at 30° C. in vacuum until constant weight is achieved.

Molecular weight and molecular weight distributions are determined by size exclusion chromatography (SEC) on a HP 1090 liquid chromatograph (software: winGPC/Polymer Standard Services, Mainz, Germany) using THF as eluent and a column combination calibrated with narrow polystyrene standards (Polymer Laboratories). The results are given in Table 7.

TABLE 7

| NOR of | Temp. [° C.] | mol % NOR | n-BuA Conv. [%] | Mn (calc.) | Mn (GPC) | Mw (GPC) | Mw/Mn (GPC) |
|---|---|---|---|---|---|---|---|
| example A20 | 130 | 1 mol % | 45 | 6217 | 6761 | 8095 | 1.20 |
| example A20 | 130 | 0.1 mol % | 41 | 52856 | 45900 | 56710 | 1.24 |

TABLE 7-continued

| NOR of | Temp. [° C.] | mol % NOR | n-BuA Conv. [%] | Mn (calc.) | Mn (GPC) | Mw (GPC) | Mw/Mn (GPC) |
|---|---|---|---|---|---|---|---|
| example A19 | 130 | 1 mol % | 54 | 7373 | 7046 | 8574 | 1.22 |
| example A19 | 130 | 0.1 mol % | 35 | 45731 | 39070 | 47090 | 1.21 |
| example A22 | 130 | 1 mol % | 61 | 8233 | 8137 | 9762 | 1.20 |
| example A22 | 130 | 0.1 mol % | 60 | 77326 | 57120 | 72870 | 1.28 |

EXAMPLE B8

Anionic Polymerization and Termination of Isoprene with the Compound of Example A2

To 10.2 g (0.15 mol) isoprene dissolved in 50 ml dry toluene in a dried ampule with teflon valve equipped with a magnetic stir bar are added in a dry argon atmosphere 3.34× $10^{-3}$ mol sec.-butyllithium (1.3 mol/L solution in cyclohexane, Fluka) and stirred for 18 hours at room temperature to allow polymerization. Subsequently a sample of the resulting prepolymer is drawn via syringe, dried at room temperature in vacuo and submitted to GPC. To the residual, slightly yellow polyisoprene solution is slowly added a calculated amount of the compound of example A2 (1.2 and 1.5 fold molar excess with respect to the initial molar amount of sec.-butyllithium used) (dissolved in toluene and degassed) via syringe. The mixture is allowed to react for another 6 hours at room temperature. Subsequently the termination reaction is quenched adding a few ml of degassed methanol. Volatiles are removed in vacuo and the resulting polyisoprene is obtained as a slight yellow rubber after drying at room temperature in vacuo until constant weight is achieved. Molecular weights are determined by GPC on a HP 1090 equipped with a RI and DMD (set at 254 nm) detector with THF as eluent (1 ml/min), using PS standards for calibration.

| Ex. | terminating agent of example A2 | conversion isoprene (%) | $M_n$ (calc.) (prepolymer) | $M_n$ (GPC) (RI detection) prepolymer/polymer after reaction | | $M_w/M_n$ prepolymer/polymer after reaction | |
|---|---|---|---|---|---|---|---|
| 1 | 1.2× excess | 93 | 2800 | 2700* | 3500** | 1.23* | 1.16** |
| 2 | 1.5× excess | 81 | 2400 | 2600* | 3300** | 1.20* | 1.14** |

*polymer before termination with the compound of example A2
**polymer after termination with the compound of example A2

Reinitiation of Terminated Polyisoprene with Styrene (Terminating Agent is Compound of Example A2)

In a dried, argon purged Schlenk tube equipped with an argon inlet and a magnetic stir bar, 5 g of samples 1 and 2 above are dissolved in 25 g of freshly distilled styrene each. The solutions are degassed by two consecutive freeze-thaw cycles and immersed in an oil bath at 120° C. to allow polymerization. After 6 hours, residual monomer is removed in vacuo and the resulting polymer is dried in vacuo at 70° C. until constant weight is achieved. Molecular weights are determined as described before.

| example | macro-initator used | conversion styrene (%) | $M_n$ (initial) | $M_n$ (block-copolymer) | $M_w/M_n$ |
|---|---|---|---|---|---|
| 3 | 1 | 24 | 3500 | 5900 | 1.27 |
| 4 | 2 | 24 | 3300 | 4400 | 1.34 |

The invention claimed is:

1. A compound 7,7,9,9-Tetramethyl-8-[1-(4-oxiranyl-methoxy-phenyl)-ethoxy]-1,4-dioxa-8-aza-spiro[4.5]decane; or 3,3,8,8,10,10-Hexamethyl-9-[1-(4-oxiranyl-methoxy-phenyl)-ethoxy]-1,5-dioxa-9-aza-spiro[5.5]undecane.

* * * * *